(12) United States Patent
Niazi et al.

(10) Patent No.: US 9,463,184 B2
(45) Date of Patent: Oct. 11, 2016

(54) CALCIUM FLUX AGONISTS AND METHODS THEREOF

(71) Applicant: Nant Holdings IP, LLC, Los Angeles, CA (US)

(72) Inventors: Kayvan Niazi, Los Angeles, CA (US); Shahrooz Rabizadeh, Los Angeles, CA (US); Justin Golovato, Los Angeles, CA (US); Patrick Soon-Shiong, Los Angeles, CA (US); Anne-Laure Le Ny, South Pasadena, CA (US); Oleksandr Buzko, Los Angeles, CA (US)

(73) Assignee: Nant Holdings IP, LLC, Culver City, CA (US)

( * ) Notice: Subject to any disclaimer, the term of this patent is extended or adjusted under 35 U.S.C. 154(b) by 0 days.

(21) Appl. No.: 14/442,392

(22) PCT Filed: Nov. 13, 2013

(86) PCT No.: PCT/US2013/069939
§ 371 (c)(1),
(2) Date: May 12, 2015

(87) PCT Pub. No.: WO2014/078447
PCT Pub. Date: May 22, 2014

(65) Prior Publication Data
US 2015/0297572 A1    Oct. 22, 2015

Related U.S. Application Data

(60) Provisional application No. 61/725,881, filed on Nov. 13, 2012.

(51) Int. Cl.
| | |
|---|---|
| A01N 43/76 | (2006.01) |
| A61K 31/42 | (2006.01) |
| A01N 43/08 | (2006.01) |
| A61K 31/34 | (2006.01) |
| A01N 43/20 | (2006.01) |
| A01N 43/24 | (2006.01) |
| A61K 31/335 | (2006.01) |
| A61K 31/423 | (2006.01) |
| A61K 31/05 | (2006.01) |
| A61K 31/12 | (2006.01) |
| A61K 31/365 | (2006.01) |
| A61K 31/404 | (2006.01) |
| A61K 31/407 | (2006.01) |
| A61K 33/24 | (2006.01) |
| A61K 9/00 | (2006.01) |
| A61K 47/06 | (2006.01) |
| A61K 47/10 | (2006.01) |
| A61K 31/341 | (2006.01) |
| A61K 31/16 | (2006.01) |
| A61K 31/66 | (2006.01) |

(52) U.S. Cl.
CPC .......... *A61K 31/423* (2013.01); *A61K 9/0014* (2013.01); *A61K 31/05* (2013.01); *A61K 31/12* (2013.01); *A61K 31/16* (2013.01); *A61K 31/341* (2013.01); *A61K 31/365* (2013.01); *A61K 31/404* (2013.01); *A61K 31/407* (2013.01); *A61K 31/66* (2013.01); *A61K 33/24* (2013.01); *A61K 47/06* (2013.01); *A61K 47/10* (2013.01)

(58) Field of Classification Search
None
See application file for complete search history.

(56) References Cited

PUBLICATIONS

ISA/KR, International Search Report and Written Opinion, Int'l Appln No. PCT/US2013/069939, dated Feb. 18, 2014 (18 pages).
Lyakh, L. A. et al., "Bacterial lipopolysaccharide, TNF-a, and calcium ionophore under serum-free conditions promote rapid dendritic cell-like differentiation in CD14+ monocytes through distinct pathways that activate NF-KB", The Journal of Immunology, 2000, vol. 165, No. 7, pp. 3647-3655.
Akira, S. et al., "Pathogen recognition and innate immunity", Cell, 2006, vol. 124, pp. 783-801.
Ulevitch, R. J., "Therapeutics targeting the innate immune system." Nature Reviews Immunology, 2004, vol. 11, pp. 512-520.
Jiang. Q. et al., "Cutting edge: lipopolysaccharide induces physical proximity between CD14 and toll-like receptor 4 (TLR4) prior to nuclear translocation of NF-KB", The Journal of Immunology, 2000, vol. 165, No. 7, pp. 541-3544.
Song, J. et al., "A novel TLR4-mediated signaling pathway leading to IL-6 responses in human bladder epithelial cells", PLoS Pathogens. 2007, vol. 3, No. 4, Article No. e60.

*Primary Examiner* — Jeffrey H Murray
(74) *Attorney, Agent, or Firm* — Fish & Tsang, LLP

(57) ABSTRACT

Calcium flux agonists are used to enhance a TLR- or NOD-mediated stimulus and to so increase an immune response of a host and reduce healing time. Preferred calcium flux agonists include $Ca^{2+}$ ionophores and SERCA inhibitors and are used in synergistic quantities where a ligand to a TLR or NOD receptor is present.

13 Claims, 14 Drawing Sheets

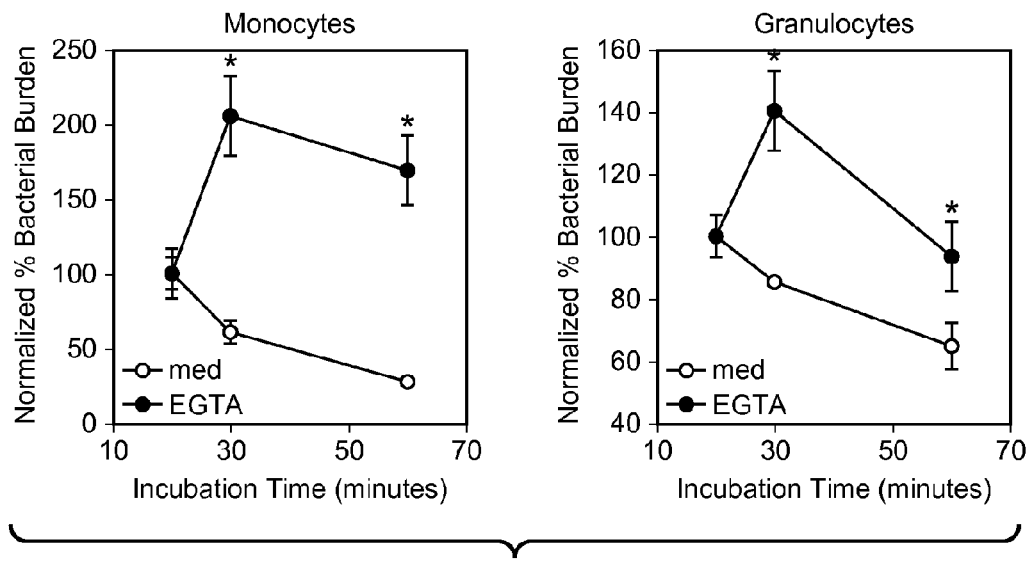
FIG. 6
FIG. 7
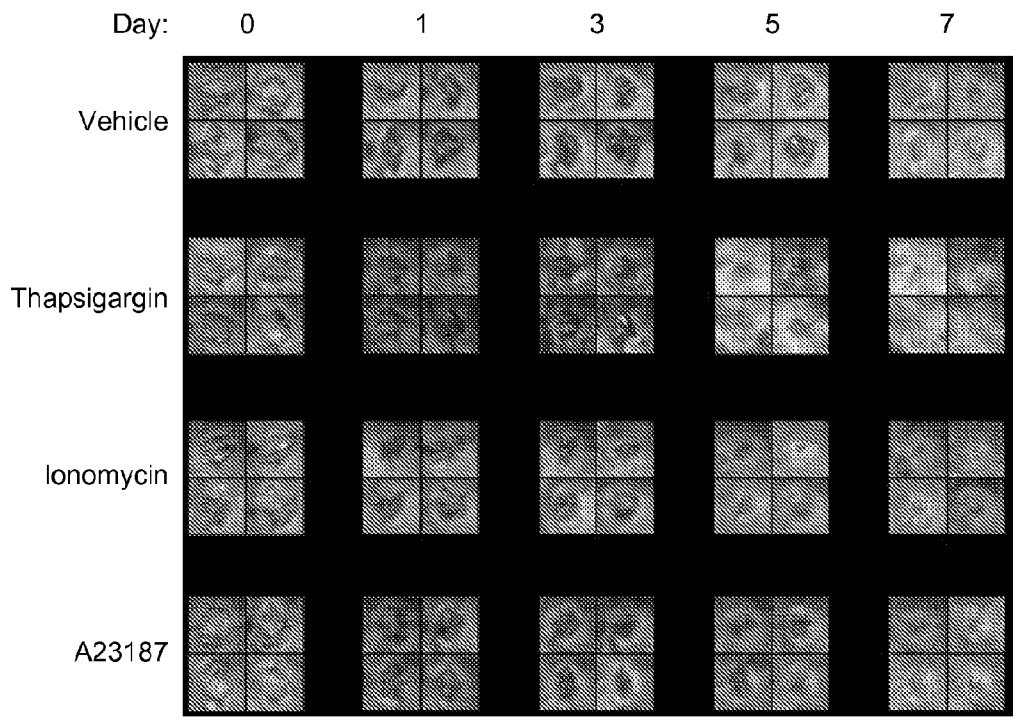

Ionomycin

Time Post Drug Addition

* p<0.05 by T test

CALCIUM FLUX AGONISTS AND METHODS THEREOF

This application claims priority to our provisional application with Ser. No. 61/725,881, filed 13 Nov. 2012, and which is incorporated by reference herein.

FIELD OF THE INVENTION

The field of the invention is compositions and methods of pharmaceutical compounds, and especially of topically applied calcium flux agonists.

BACKGROUND OF THE INVENTION

Various calcium flux agonists are known in the art and have vastly different origins. For example, certain compounds act as ionophores and typically raise intracellular calcium levels by importing calcium ions into the cell, while other compounds raise intracellular calcium levels by increasing calcium secretion from intracellular stores like the endoplasmic reticulum and mitochondria.

Among various other known ionophores, calcimycin (A23187) and ionomycin are natural products (from the Gram+ bacteria *Streptomyces chartreusensis* and *Streptomyces conglobatus*, respectively) which were initially described as antibiotics decades ago. More specifically, both A23187 and ionomycin demonstrate direct antibiotic activity against a variety of potential microbial pathogens as was reported in U.S. Pat. No. 3,960,667 and U.S. Pat. No. 3,873,693. Unlike classical antibiotics (e.g., penicillin or tetracycline) that inhibit biochemical pathways specific to microbial proliferation such as bacterial cell wall synthesis or bacterial ribosome function, A23187 and ionomycin belong to a separate class of antibiotic compounds that bind divalent cations as substrates with relatively high specificity. For example, A23187 binding affinity is characterized by $Mn^{2+}>Ca^{2+}=Mg^{2+}>Sr^{2+}>Ba^{2+}$ while ionomycin is characterized by $Ca^{2+}>Mg^{2+}>Ba^{2+}>Sr^{2+}$.

On the other hand, thapsigargin is a typical ER secretagogue and can be characterized as a sesquiterpene lactone. Thapsigargin is isolated from a plant (*Thapsia garganica*) and acts as a non-competitive inhibitor of various sarco/endoplasmic reticulum Ca2+ ATPases (SERCA). Thapsigargin:SERCA binding demonstrates an affinity constant in the low picomolar range and is toxic to both dividing and non-dividing cells. In animals, limited skin contact with thapsigargin can result in inflammation and chronic repetitive topical exposure can result in non-malignant papilloma formation when used in conjunction with a strong DNA damaging agent. In addition to thapsigargin (and structural analogs like thapsigargicin, etc.), other SERCA inhibitors include cyclopiazonic acid (CPA) and 2,5-di-tert-butylhydroquinone (DBHQ).

Difficult-to-treat skin infections represent an emerging public health concern for several reasons including the ever-increasing number of diabetic patients suffering from chronic skin ulcers, the presence of antibiotic resistant microbial flora (e.g., methicillin-resistant *Staphylococcus aureus* or MRSA), and the increasing frequency of outbreaks of necrotizing fasciitis (or "flesh-eating bacteria disease"). In addition to bacteria, many fungi and viruses can also cause significant infections of the skin. Although antibiotics remain the best treatment option for many of these disorders, it would be desirable to stimulate a patient's own cells and their associated functions to further improve patient recovery from ongoing infections and possibly even to stimulate long-term immunity against the offending organism to limit pathogenesis upon subsequent encounter.

In higher organisms, epithelial tissues including the skin serve as a critical barrier against pathogen-based, chemical, and physical insults. The epidermal layer of skin is comprised of keratinocytes, immune cells such as Langerhans cells and CD8$^+$ T cells, Merkel cells and melanocytes. In addition to Langerhans cells, which are a subtype of dendritic cells (DC) responsible for disease surveillance, keratinocytes (which account for ~95% of the total epidermal population) also serve as immune sentinels through their expression of various pattern recognition receptors such as members of the toll-like receptor (TLR) proteins, C-type lectin receptors (CLR), inflammasomes, etc.

Activation of these receptors in keratinocytes by their cognate ligands results in the release of both chemokines such as interleukin-8 (IL-8), CCL2, and CCL20 to recruit other immune cells as well as immune-regulating cytokines such as TGF-β and IL-10. Below the epidermis, the dermis is comprised of a larger variety of cell types including various subsets of CD4$^+$ (Th1, Th2, Th17, etc) and non-classical (e.g. γδ, NK-, etc.) T lymphocytes, various antigen presenting cells (such as macrophages and dermal and plasmacytoid DC), mast cells and fibroblasts many of which express the various pattern recognition proteins described above. As such, both epidermal and dermal cells cooperate to prevent microbial invasion or other physical insults that could lead to significant disease.

The TLR proteins (TLR 1-10 in man) are type I membrane proteins which serve as pattern recognition receptors (PRR) for specific classes of ligands associated with disease and tissue homeostasis and as such are expressed on a variety of immune and non-immune cell types alike. As with all receptors, TLR signal transduction is triggered by ligand binding, and ligands may be grouped into pathogen-associated molecular patterns (or PAMP) and disease-associated molecular patterns (DAMP).

TLR-recognized PAMP include bacterial lipoproteins/lipopeptides, liposaccharides, flagellin, and unmethylated CpG DNA, fungal cell wall components (e.g. zymosan), and viral nucleic acids (dsRNA, ssRNA, and CpG DNA), while DAMPS are derived directly from the host, can occur in the absence of infection, and are recognized predominantly by only two members of the TLR family of proteins (either TLR2 and/or TLR4).

Once activated by their appropriate ligands, TLR initiate signaling cascades which serve both to limit the extent of infection/disease and to trigger tissue repair. With regards to the latter, TLR ligand recognition results in the up-regulation of antimicrobial activity and causes the activation/maturation of various immunological players to complete the destruction of the invading pathogen. For example, TLR activation can result in the release of reactive oxygen species (ROS), antimicrobial peptides, and upregulation of phagocytic function in innate cells such as macrophages, neutrophils, keratinocytes, etc. In addition to their role in combating disease, TLRs are also involved in tissue repair and regeneration as demonstrated in various models of tissue damage (including those induced by chemical, radiation, surgical, and infectious injury).

A further class of pattern recognition receptors is formed by the NOD-like receptor protein family, and includes NOD1 and NOD2 as the most prominent members. NOD1 and NOD2 are intracellular pattern recognition receptors, which are similar in structure to resistance proteins of plants, and mediate innate and acquired immunity by recognizing bacterial molecules containing D-glutamyl-meso-diaminopimelic acid and muramyl dipeptide, respectively. Following stimulation by their respective ligands, both NOD proteins interact with RIPK2 through respective recognition domains, which ultimately results in activation of the transcription factor NF-κB.

Previous efforts to characterize the response of intact skin to topical application of small molecule agonists of signal transduction (such as the protein kinase C agonist TPA/PMA or sustained calcium flux agonists like A23187, ionomycin, or thapsigargin) demonstrated a spectrum of downstream results. For example, topical application of the phorbol ester TPA caused vasodilation, microvascular permeability alterations, inflammatory cell recruitment, and the release of pro-inflammatory factors from various cell types. In contrast to PKC agonists, topical treatment with sustained calcium flux agonists (SCFA) resulted in skin inflammation and hyper-proliferation. On the other hand, exposure of cells to the TLR ligand (LPS) in the presence of relatively high quantities of a calcium ionophore (ionomycin) did not lead to any measurable immunostimulatory effect (Proc Natl Acad Sci USA. 2012 Jul. 10; 109(28): 11282-7). When applied individually at relatively high dosages, calcium ionophores and TLR ligands are known to stimulate differentiation or to activate dendritic cells as discussed in US 2012/0272700A1 and US 2013/0183343A1.

Therefore, while numerous compositions and uses for calcium flux agonists and/or ligands for TLR/NOD are known in the art, there is still a need to provide compositions and methods that provide improved immunomodulatory activity.

SUMMARY OF THE INVENTION

The present inventive subject matter is drawn to various compositions and methods of calcium flux agonists in which these compounds are used to modulate an immune response to a TLR- or NOD-mediated event, and especially to synergistically increase responses to TLR and/or NOD ligand binding. Notably, synergistic effect with respect to immune stimulation is observed where the calcium flux agonist is present in suboptimal concentrations.

Viewed from a different perspective, the inventors contemplate use of calcium flux agonists to amplify intracellular $Ca^{2+}$ dependent TLR/NOD signaling. Therefore, and among other suitable uses, especially contemplated uses include pre-conditioning of tissue to allow for an enhanced response to a TLR/NOD-dependent stimulus (e.g., infection or injury), and/or treatment of topical or other infections of the epithelium with calcium flux agonists to amplify intracellular $Ca^{2+}$ dependent TLR/NOD signaling. Consequently, the inventors also contemplate topical pharmaceutical and cosmetic compositions for prevention and/or treatment of skin infections and other conditions (e.g., diabetic ulcers) to stimulate wound healing, and/or to decrease scarring.

In one aspect of the inventive subject matter, the inventors contemplate use of a calcium flux agonist to enhance an immune response of an immune competent cell to a ligand of a pattern recognition receptor. For example, where the calcium flux agonist is a calcium ionophore, preferred agonists include ionomycin, calcimycin, beauvericin, calcium ionophore II, calcium ionophore IV, calcium ionophore V, and calcium ionophore VI, and where the agonist is a SERCA inhibitor, preferred SERCA inhibitors include DBHQ (2,5-di-tert-butylhydroquinone), thapsigargin, ruthenium red, gingerol, paxilline, and cyclopiazonic acid. Among other phenomena observable, the enhanced immune response is typically evidenced by an increased IL-8 secretion and/or an increased activation of NF-κB signaling, and it is preferred that the immune response is synergistically enhanced by the calcium flux agonist in the presence of the ligand, particularly where the calcium flux agonist is used at a suboptimal concentration (with respect to a maximum effect of the calcium flux agonist in the absence of the ligand).

With respect to suitable cells it is generally contemplated that the cells are immune competent cell, which will preferably reside in the epidermal or dermal layer of skin. Moreover, the immune competent cells will generally express a TLR receptor and/or a NOD receptor as the pattern recognition receptor. Thus, ligands will typically include PAMP and DAMP ligands.

Consequently, the inventors also contemplate use of a calcium flux agonist in the manufacture of a topically applied medicament to enhance an immune response in skin. In such uses, the immune response is generally associated with binding of a (PAMP or DAMP) ligand to a pattern recognition receptor in an immune competent cell, and the pattern recognition receptor is most typically a TLR receptor or a NOD receptor. As noted above, preferred calcium flux agonists include calcium ionophores (e.g., ionomycin, calcimycin, calcium ionophore II, calcium ionophore IV, calcium ionophore V, or calcium ionophore VI), and SERCA inhibitors (e.g., 2,5-di-tert-butylhydroquinone, thapsigargin, ruthenium red, gingerol, paxilline, or cyclopiazonic acid, etc.), and/or the calcium flux agonist is present in the medicament at a concentration such that the agonist is present in the cell in the presence of the ligand at a suboptimal concentration.

Consequently, and viewed from a different perspective, the inventors also contemplate use of a calcium flux agonist in the manufacture of a topically applied medicament to enhance wound healing of skin. In such uses, the calcium flux agonist is typically present in an amount effective to activate NF-κB signaling of cells in the wound. Such uses are particularly advantageous where the wound is infected with a bacterial pathogen (typically expressing or producing a ligand for a TLR receptor and/or a NOD receptor).

In yet another aspect of the inventive subject matter, the inventors also contemplate a pharmaceutical composition that comprises a calcium flux agonist (e.g., calcium ionophore or a SERCA inhibitor) in a pharmaceutically acceptable carrier, wherein the pharmaceutical composition is formulated for topical application to injured or infected skin, and wherein the calcium flux agonist is present in an amount that enhances, upon application of the formulation to the injured or infected skin, an immune response of an immune competent cell in the injured or infected skin to a ligand of a pattern recognition receptor (e.g., TLR receptor or NOD receptor). While such pharmaceutical compositions may be formulated, for example, as a liquid, a spray, or a gel, it is also contemplated that the pharmaceutical composition is formulated for topical application to injured or infected skin via a solid carrier that is applied to the injured or infected skin (e.g., wound dressing or band aid impregnated with the pharmaceutical composition). For example, the skin may be infected with a (e.g., bacterial) pathogen that comprises a ligand for a TLR receptor or a NOD receptor.

In particularly preferred pharmaceutical compositions, the amount of the calcium flux agonist (e.g., ionomycin, calcimycin, or thapsigargin) synergistically enhances the immune response in the presence of the ligand as compared to the immune response in the absence of the ligand.

Therefore, the inventors also contemplate a method of enhancing an immune response of a cell expressing a pattern recognition receptor (e.g., TLR receptor or a NOD receptor) to a ligand (e.g., PAMP) of the pattern recognition receptor, wherein the method includes a step of exposing the cell in the presence of the ligand to a calcium flux agonist (e.g., SERCA inhibitor or calcium ionophore) in an amount that enhances the immune response.

Most typically, the immune response is evidenced as an increased IL-8 secretion and/or an increased activation of NF-κB signaling, and it is especially preferred that the ligand and the calcium flux agonist are present in synergistic quantities. While not limiting to the inventive subject matter, it is further preferred that the cell is located in a dermal layer or epidermal layer of skin (e.g., injured or infected skin).

Viewed from a different perspective, the inventors therefore also contemplate a method of treating injured or infected skin in which in one step the injured or infected skin is contacted with a calcium flux agonist (e.g., calcium ionophore or a SERCA inhibitor) in an amount that enhances an immune response (e.g., increased IL-8 secretion or increased activation of NF-κB signaling) and that increases wound healing.

Thus, the inventors also contemplate a method of modulating an immune response to a TLR- or NOD-mediated stimulus in a tissue (e.g., epithelial tissue) or cell, in which in one step the tissue or cell is contacted (e.g., topically applied) with a calcium flux agonist at a concentration effective to increase an intracellular calcium concentration as compared to an intracellular calcium concentration without the calcium flux agonist. Most typically, the concentration of the calcium flux agonist (e.g., calcium ionophore or SERCA inhibitor) is effective to modulate the immune response to the TLR-mediated stimulus. In some aspects of the inventive subject matter, the TLR- or NOD-mediated stimulus is a bacterial, viral, or fungal infection, while in other aspects the TLR- or NOD-mediated stimulus is a tissue injury.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIG. 3B: Ionomycin; FIG. 3C: Cyclopiazonic acid; FIG. 3D: DBHQ; FIG. 3E: Thapsigargin) and exemplary TLR and NOD ligands for respective TLR and NOD receptors with respect to strength of IL-8 production.

FIG. 6 shows graphs illustrating the requirement of human primary monocytes and granulocytes for extracellular $Ca^{2+}$ for optimal killing of phagocytosed S. aureus.

FIG. 7 shows photographs of wound healing using selected calcium flux agonists.

DETAILED DESCRIPTION

Figure 1A:
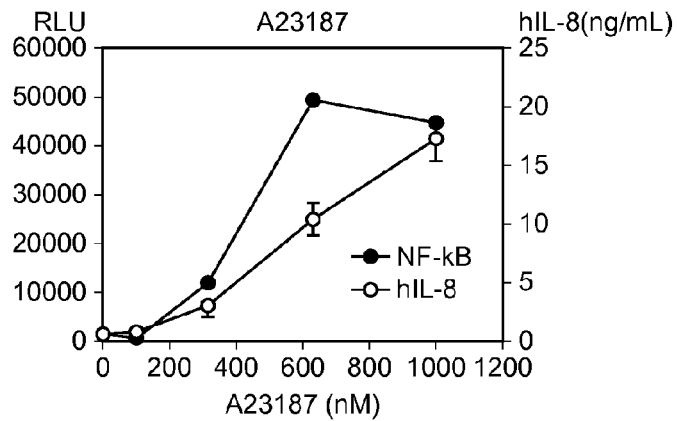
FIGS. 1A-1C are graphs depicting the dose response curves for various calcium flux agonists (1A: A23187; 1B: Ionomycin; 1C: Thapsigargin) with respect to strength of NF-κB signaling and IL-8 production.

The inventors have discovered that calcium flux agonists that increase intracellular free $Ca^{2+}$ concentration (especially calcium ionophores and SERCA inhibitors) can be effectively used to modulate and/or enhance the immune response of a host to a TLR- or NOD-mediated event. In a particularly notable aspect, calcium flux agonists synergistically increased host responses to TLR and/or NOD ligand binding where the calcium flux agonist is present in a substantial suboptimal concentration.

Indeed, the inventors have discovered as further detailed below that innate immune cells help to control infection by recognizing S. aureus bacteria or their shed products (and other pathogens and pathogen fragments) in a $Ca^{2+}$-dependent manner to become activated, which can then be effectively augmented by exposure of the affected cells to suboptimal doses of $Ca^{2+}$+ flux agonists. Since many common pathogen (e.g., S. aureus) products are predominantly recognized by TLR and NOD receptors, the inventors investigated and also confirmed that pathogen products are indeed activating and that such activation can be further significantly enhanced using numerous $Ca^{2+}$ flux agonists (which can be abrogated or substantially reduced by calcium chelating agents). Moreover, the inventors also demonstrated that $Ca^{2+}$ is a critical factor in human monocytes and granulocytes (especially neutrophils) for effective killing of phagocytosed bacteria. Such findings also directly translated into a mammalian (murine) model of skin infection and wound healing following live infection.

In one aspect of the inventive subject matter, the inventors therefore contemplate various compositions and methods for (typically topical) treatment and/or prophylaxis that are effective in stimulating the host cells' capability of immune response to a pathogen and that are effective in reducing scarring and time-to-closure of a topical wound, especially where the wound is infected with one or more pathogens that express or otherwise comprise a ligand for TLR and/or NOD. For example, the inventors contemplate topical application of a SERCA inhibitor (e.g., thapsigargin) and/or an ionophore (e.g., ionomycin and/or A23187 (calcimycin) to prevent or treat a superficial skin infection (e.g., bacterial infection).

In that context, the inventors discovered that topical application of SERCA inhibitors and/or ionophores greatly decreased bacterial burden in superficial skin infections (e.g., S. aureus) with concomitant improvement in wound healing kinetics in a live animal infection model. Remarkably, the antibacterial effect was not (in the case of the SERCA inhibitor thapsigargin) or not entirely (in the case of ionophores) attributable to a direct antibiotic effect where the calcium flux agonist acted as a biocide against the pathogen, but rather to the role of the calcium flux agonists as an immunological adjuvant. While not wishing to be bound by any theory or hypothesis, the inventors contemplate that the antibacterial effect may be due to synergistic activation of cytokine release and activation of the nuclear factor-κB (NF-κB) signaling pathway when calcium flux agonists were provided in the presence of TLR or NOD ligands.

Even more remarkable, very strong synergy between TLR and/or NOD activation and calcium flux agonists (ionophores/SERCA inhibitors) was observed for IL-8 production and activation of NF-κB signaling. For example, human promonocytic THP-1 cells were incubated in the presence or absence of a suboptimal dose of the TLR2 ligand Pam2CSK4 and compared to similarly treated cells which also received suboptimal doses of ionophore (here: A23187 and ionomycin). Interestingly and as further shown in more detail below, the inventors found that both agonists significantly increased the amount of IL-8 produced beyond the levels that would be produced if the individual responses were cumulative, thus indicating true synergy. In another example, κB-LUC THP-1 cells (a THP-1-derived transfectant line harboring an NF-κB-driven luciferase expression cassette) were cultivated in the presence or absence of a suboptimal dose of the TLR2 ligand Pam2CSK4 and compared to similarly treated cells that also received suboptimal doses of various SERCA inhibitors. Notably, and as also shown in more detail below, the inventors found that all of the tested agonists (here: thapsigargin, cyclopiazonic acid) significantly increased the amount of luciferase produced beyond levels that would be produced if individual responses were cumulative and so once more indicate synergy.

In that context it should be noted that NF-κB impacts adaptive immunity through its involvement in mediating cellular activation, inflammatory cytokine secretion, proliferation, and survival, while IL-8 is a powerful chemoattractant for immune cells like neutrophils, an innate immune cell type critical for antibacterial and antifungal responses. Interestingly, ligand activation of TLR4 in the presence of the $Ca^{2+}$ flux inducing agent ionomycin results in the synergistic production of arachidonic acid-derived eicosanoid lipids in a mouse macrophage line, indicating the possibility of combining $Ca^{2+}$ flux inducing agents with TLR ligands for preventative and curative effects.

The inventors therefore contemplate in one aspect of the inventive subject matter that ionophores (e.g., A23187 and/or ionomycin) will produce a synergistic effect in vivo with infection/disease associated TLR and/or NOD ligands to alter in situ immune cell response and repair processes. Such effects are readily ascertained as the inventors demonstrated in more detail below by use of topically-applied formulations containing various ionophores to alter the course of superficial skin infection, for example, induced by S. aureus as a model system, using bacterial burden and wound size as indicators of prophylactic and/or therapeutic success.

Similarly, the inventors also contemplate in another aspect of the inventive subject matter that thapsigargin (and various other SERCA inhibitors) produce a synergistic effect in vivo with infection/disease associated TLR and/or NOD ligands to alter in situ immune cell and repair processes in vivo. As noted above, such effects are readily ascertained as the inventors demonstrated in more detail below by use of topically-applied formulations that contain various SERCA inhibitors (and especially thapsigargin) to alter the course of superficial skin infection, for example, induced by S. aureus as a model system, using bacterial burden and wound size as indicators of prophylactic and/or therapeutic success.

Therefore, it should be appreciated that the inventors especially contemplate use of a calcium flux agonist to enhance the immune response of one or more immune competent cells to a ligand of a pattern recognition receptor. Most typically, suitable immune competent cells are cells that are part of the cellular immune system (e.g., a B-cell, a T-cell, an antigen-presenting cell or innate sentinel cell, and especially dendritic cells, macrophages, mast cells, monocytes, etc.), and it is generally preferred that such immune competent cells are in the dermal or epidermal layer of skin. Consequently, the inventors also contemplate the use of a calcium flux agonist to manufacture a topically applied medicament to enhance an immune response and/or wound healing (e.g., reduce time-to-closure) in skin. In such uses, it is generally contemplated that the immune response is associated with binding of a ligand to a pattern recognition receptor in an immune competent cell. Among other pattern recognition receptors, especially suitable pattern recognition receptors include those of the TLR and NOD families, and especially TLR1, TLR2, TLR3, TLR4, TLR5, TLR6, TLR7, TLR8, TLR9, TLR10, TLR11, TLR12, and TLR13, as well as NOD1, NOD2, NOD3, NOD4, NOD5, and CIITA. Therefore, it should be appreciated that the ligand may vary considerably, and contemplated ligands include all ligands known to bind to the TLR and/or NOD receptors, and most preferably pathogen-associated molecular pattern ligands (PAMP) and damage/disease-associated molecular pattern ligands (DAMP). Consequently, suitable PAMP ligands will include various lipopeptides, glycolipids, lipoteichoic acid, heat shock proteins, beta-glucans, fibrinogen, heparin sulfate fragments, hyaluronic acid fragments, RNA (and esp. ssRNA), DNA (and csp. CpG sequences), profiling, etc. Likewise, suitable DAMPs will include various nuclear and/or cytosolic proteins, and especially heat shock proteins, HMGB1, DNA, RNA, and fragments of proteins derived from extracellular matrix.

In yet another aspect of the inventive subject matter, the inventors also contemplate a method of enhancing an immune response of a cell (that expresses one or more of the pattern recognition receptors noted above) to a ligand of the pattern recognition receptor. As noted above, the nature of the ligand will predominantly depend on the type of receptor, and all receptors and ligands as discussed above are suitable for contemplated methods. In especially preferred methods, the cell is exposed in the presence of the ligand to a calcium flux agonist in an amount that enhances the immune response. Of course, it should be noted that the ligand may be delivered (e.g., together with the calcium flux agonist) as part of a treatment regimen. However, and more typically, the ligand will be provided by a pathogen that is present in or near the cell, or provided by the host as a DAMP. While not limiting to the inventive subject matter, the enhanced immune response will typically be characterized by at least one of an increased IL-8 production and an increased NF-κB signaling (e.g., increased expression of a gene under the control of NF-κB in the presence of the calcium flux agonist as compared to the expression of the same gene in the absence of the calcium flux agonist). As is readily evident from the experimental details below, the enhanced immune response is typically a synergistic increase.

Therefore, the inventors also contemplate a method of (prophylactic) treating injured or infected skin by contacting the injured or infected skin with a calcium flux agonist in an amount that enhances an immune response and that increases wound healing as further shown in more detail below. Viewed from a different perspective, it should thus be appreciated that one or more calcium flux agonists can be employed to modulate an immune response to a TLR- or NOD-mediated stimulus in a tissue or cell.

Contemplated Calcium Flux Agonists

Compounds contemplated suitable for use herein are generally deemed to be useful for prophylaxis and/or treatment of various infectious diseases and trauma, and especially with infectious disease of the skin or other epithelium, particularly where the host response to the disease and/or trauma is associated with a TLR or NOD response pathway. Therefore, it is generally preferred that the compounds according to the inventive subject matter will be calcium flux mediators (and especially agonists) that lead to an at least temporary, and more typically sustained increase of intracellular calcium.

Therefore, especially preferred compounds include ionophores and SERCA inhibitors well known in the art. Most preferably, suitable ionophores are calcium ionophores, and especially ionomycin, calcimycin, calcium ionophore II, calcium ionophore IV, calcium ionophore V, or calcium ionophore VI, while particularly preferred SERCA inhibitors include 2,5-di-tert-butylhydroquinone (DBHQ), thapsigargin, ruthenium red, gingerol, paxilline, or cyclopiazonic acid. It should also be noted that while the above is a list of preferred compounds, the list is not exhaustive, and individual compounds may be combined to form a mixture of two or more calcium flux agonists (e.g., to provide an extracellular and intracellular agonist), and/or additional compounds may be added.

Of course, it should be appreciated that (where appropriate) contemplated compounds may have one or more asymmetric centers or groups that may give rise to isomeric, tautomeric, or other steric isoforms (e.g., R-, and/or S-configuration, E/Z configuration, tautomeric isoforms, enantiomers, diastereomers, etc.), and each of such forms and mixtures thereof are expressly contemplated herein. Additionally, it should be appreciated that contemplated calcium flux agonists may be chemically modified to achieve a desired physicochemical parameter (e.g., solubility in aqueous solvents, membrane permeability, selectivity towards $Ca^{2+}$, etc.) Therefore, suitable calcium flux agonists may be fully synthetic, semi-synthetic, or isolated from host strains producing such ionophores.

Moreover, contemplated compounds may also be converted to prodrugs to increase delivery and/or target specificity to an affected tissue or organ. The term "prodrug" as used herein refers to a modification of contemplated compounds, wherein the modified compound exhibits less pharmacological activity (as compared to the unmodified compound) and wherein the modified compound is converted within a target cell or target organ back into the unmodified form. For example, conversion of contemplated compounds into prodrugs may be useful where the active drug is too toxic for safe systemic administration, or where the contemplated compound is poorly absorbed by the digestive tract, or where the body breaks down the contemplated compound before reaching its target. There are numerous methods for the preparation of prodrugs known in the art, and all of those are contemplated herein. For example, suitable prodrug approaches are described in Prodrugs (Drugs and the Pharmaceutical Sciences: a Series of Textbooks and Monographs) by Kenneth B. Sloan (ISBN: 0824786297), or in Hydrolysis in Drug and Prodrug Metabolism: Chemistry, Biochemistry, and Enzymology by Bernard Testa (ISBN: 390639025X), which are to the appropriate extent incorporated by reference herein.

Similarly, it should be noted that contemplated compounds may also be less active in the form as described herein, and be more active as metabolite or metabolites that are formed in vivo. For example, contemplated compounds may be transformed by the hepatic phase I and/or phase II enzyme system, or by gastric acidity, intestinal microbial environment, or other biochemical process. Thus, suitable compounds may be oxidized, hydroxylated, ligated to a carbohydrate, etc.

Contemplated Compositions

It is generally contemplated that contemplated calcium flux agonists are provided in a composition that is suitable for delivery to a cell or tissue. Therefore, suitable compositions will include liquid compositions, gels, solid compositions, all of which may be associated or coupled to a carrier, or applied directly to the cell or tissue. Most typically, such compositions will include an aqueous solvent or otherwise pharmaceutically acceptable carrier together with one or more calcium flux agonists. In particularly preferred aspects of the inventive subject matter, the pharmaceutical composition is formulated for topical application to an injured or infected tissue, more preferably epithelial tissue, and most preferably skin. Moreover, it is generally preferred that the calcium flux agonist is present in an amount that enhances, upon application of the formulation to the cell or tissue, an immune response of an immune competent cell in the injured or infected cell or tissue to one or more ligands of a pattern recognition receptor (typically TLR and/or NOD receptor). It is still further preferred that the calcium flux agonist is present in an amount that synergistically enhances the immune response in the presence of the ligand as compared to the immune response in the absence of the ligand.

Therefore, it should be appreciated that the compositions according to the inventive subject matter may be administered using various routes, including topically, nasally, by inhalation, orally, parenterally, etc. wherein the term "parenteral" as used herein includes subcutaneous, intravenous, intramuscular, intraarticular, intrasynovial, intrathecal, intrahepatic, intralesional, and intracranial administration (typically injection or infusion). Most preferably, however, the compositions are administered topically in a liquid, gel, or solid form.

For example, the pharmaceutical compositions of this invention may be administered topically to areas or organs readily accessible by topical application, including the eye, the skin, the lower intestinal tract, or areas exposed during surgical intervention. There are numerous topical formulations known in the art, and all of such formulations are deemed suitable for use herein.

For example, contemplated compositions may be formulated in a suitable ointment containing the active component suspended or dissolved in one or more carriers. Carriers for topical administration of the compounds of this invention include mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include mineral oil, sorbitan monostearate, polysorbate 60, cetyl esters wax, cetearyl alcohol, 2-octyldodecanol, benzyl alcohol and water. As at least some of the active compounds are highly hydrophobic, it is contemplated that the formulation will take into account relatively poor solubility and thus may be prepared as an emulsion, as nanovesicular particles, or administered in a hydrophobic base under occlusion.

Alternatively, contemplated formulations may also be injected into skin or other site of administration. Most preferably, sterile injectable forms of contemplated compounds will include emulsions, aqueous solutions, or oleaginous suspensions. These suspensions may be formulated according to techniques known in the art using suitable dispersing or wetting agents and suspending agents. The sterile injectable preparation may also be prepared as a sterile injectable solution or suspension in a non-toxic parenterally acceptable diluent or solvent, for example as a solution in 1,3-butanediol. Among other acceptable vehicles and solvents, especially contemplated liquids include water, Ringer's solution, and isotonic sodium chloride solution. In addition, sterile, fixed oils may be employed as a co-solvent or suspending medium (e.g., natural or synthetic mono- or diglycerides). Fatty acids may also be used, and suitable fatty acids include oleic acid and its glyceride derivatives, olive oil, castor oil, especially in their polyoxyethylated versions. Such oil solutions or suspensions may further contain a long-chain alcohol diluent or dispersant.

In another example, contemplated compounds may be orally administered in any orally acceptable dosage form, including capsules, tablets, aqueous suspensions, or solutions. In the case of tablets for oral use, all pharmaceutically acceptable carriers (e.g., lactose, corn starch, etc) are deemed suitable. Similarly, various lubricating agents may be added (e.g., magnesium stearate). For oral administration in a capsule form, useful diluents include lactose and dried corn starch.

With respect to the amount of contemplated compounds in the composition, it should be recognized that the particular quantity will typically depend on the specific formulation, active ingredient, and desired purpose. Therefore, it should be recognized that the amount of contemplated compounds will vary significantly. However, it is generally preferred that the compounds are present in a minimum amount effective to deliver prophylactic and/or therapeutic effect in vitro and/or in vivo. Viewed from another perspective, the calcium flux agonist is typically present in an amount effective to activate NF-κB signaling and/or increase IL-8 production of cells in vitro, or in a wound or otherwise diseased (e.g., infected) tissue.

Moreover, it is generally preferred that the calcium flux agonist is provided to the cell or tissue such that the agonist will be present in the cell (in the presence of the TLR or NOD ligand) at a suboptimal concentration with respect to a maximum effect of the calcium flux agonist in the absence of the ligand. In this context, it should be noted that the suboptimal concentration of the calcium flux agonist is a concentration that is well below the maximum response (with respect to NF-κB and/or IL-8 production) obtainable with the calcium flux agonist. Thus, sub-optimal concentration of the calcium flux agonist will be concentration that will provide equal or less than 80%, equal or less than 70%, equal or less than 60%, between 20-60%, or between 10-50% of the dosage that provides a maximum effect (with respect to NF-κB and/or IL-8 production) for that calcium flux agonist. For example, as can be seen from the experimental data below, an exemplary suboptimal concentration for thapsigargin is between 10-50 nM (e.g., about 20 nM), which is well below a maximum effect obtainable for thapsigargin as can be seen from FIG. 1C. Likewise, an exemplary suboptimal concentration for A23187 is between 100-500 nM (e.g., about 316 nM), which is well below a maximum effect obtainable for A23187 as can be seen from FIG. 1A, and an exemplary suboptimal concentration for ionotnycin is between 300 nM-5 μM (e.g., about 1 μM), which is well below a maximum effect obtainable for ionomycin as can be seen from FIG. 1B. Viewed from another perspective, suboptimal concentrations will therefore be characterized as concentrations below which an acute toxic effect can be observed for a cell or tissue exposed to the calcium flux agonist.

As is shown in more detail below, maximum response and suboptimal concentrations can be readily determined using an IL-8 ELISA test and/or a luminescence test. In preferred aspects of the inventive subject matter, the suboptimal concentration will be a concentration at which the response is equal or less than 70% of the maximum response, more typically equal or less than 50% of the maximum response, and most typically equal or less than 30% of the maximum response. Thus, suboptimal concentrations will be in the range of between 1-20% of the maximum response, between 20-40% of the maximum response, between 40-60% of the maximum response, between 60-80% of the maximum response, or between 80-95% of the maximum response. Likewise, it is noted that the ligand may also be present in a suboptimal concentration, and the suboptimal concentration will be a concentration at which the response to the ligand is equal or less than 70% of the maximum response, more typically equal or less than 50% of the maximum response, and most typically equal or less than 30% of the maximum response for the ligand alone. Thus, suboptimal concentrations will be in the range of between 1-20% to 1-40% of the maximum response, between 20-40% to 20-80% of the maximum response, between 30-70% of the maximum response, between 40-80% of the maximum response, or between 50-95% of the maximum response for the ligand alone.

Consequently, in at least some embodiments, contemplated compounds are present in an amount of between about 0.1 ng/ml to about 100 mg/ml, more typically in an amount of between about 10 ng/ml to about 10 mg/ml, and most typically between about 1 μg/ml to about 100 μg/ml. Where the formulation is a solid or a gel, contemplated compounds will be present in an amount of between about 0.1 ng/g to about 100 mg/g, more typically in an amount of between about 10 ng/g to about 10 mg/g, and most typically between about 1 μg/g to about 100 μg/g. Viewed from a different perspective, the calcium flux agonist will typically be present in the formulation at a concentration of between 0.1 μM to 10 μM, between 10 μM to 100 μM, between 100 μM to 1 mM, between 1 mM to 10 mM, or between 10 mM to 100 mM. Additionally, and with respect to the concentration of the calcium flux agonist at the cell or tissue ("effective exposure concentration"), it is generally preferred that the effective exposure concentration will be between 1 μM and 1 mM, and most preferably at a suboptimal concentration for the respective calcium flux agonist. Therefore, thapsigargin will typically have an effective exposure concentration of between 1 nM to 1 μM, more typically between 1 nM to 500 nM, and most typically between 1 nM to 50 nM, while DBHQ and CPA will typically have an effective exposure concentration of between 100 nM to 500 μM, more typically between 500 nM to 100 μM, and most typically between 1 μM to 50 μM. On the other hand, ionomycin and A23187 will typically have an effective exposure concentration of between 10 nM to 100 μM, more typically between 100 nM to 50 μM, and most typically between 200 nM to 10 μM.

Therefore, suitable amounts of contemplated compounds will be in the range of 0.1 µg per dosage unit to about 0.5 gram per dosage unit, more typically between 10 µg per dosage unit to about 0.05 gram per dosage unit, and most typically between 50 µg per dosage unit to about 100 mg per dosage unit. Thus, suitable dosages will be in the range of about 0.01 µg/kg and 100 mg/kg, more typically between 1 µg/kg and 50 mg/kg, and most typically between 10 µg/kg and 10 mg/kg.

With respect to dosage units, it is generally contemplated that the dosage unit will be such that the dosage unit is effective to achieve the desired therapeutic and/or prophylactic effect. Viewed from a different perspective, a dosage unit will preferably contain sufficient quantities of the calcium flux agonist to (preferably synergistically) increase IL-8 production and/or NF-κB signaling.

It should further be appreciated that while contemplated compounds and compositions may be applied topically or in a pharmaceutical composition (e.g., cream, ointment, etc.) numerous alternative methods of application to the affected tissue are also deemed suitable. For example, contemplated compositions may be coupled to or incorporated into a carrier that is directly and reversibly applied to the site of treatment or that is implanted or otherwise placed in proximity or contact with the treatment site. For example, contemplated compounds and compositions may be incorporated into one or more portions of topically applied and removable carriers (e.g., bandages, gauze, etc.) or into covering films that may or may not dissolve or erode (e.g., via biodegradable drug-eluting polymers). Alternative carriers include beads or biodegradable drug-eluting polymers that are implanted wherein contemplated compounds and compositions may be part of the surface of the implanted device or coated onto such devices.

Dose Response of Calcium Flux Agonists

The inventors performed several studies to identify the effect of calcium flux agonists on various components of an immune response, and particularly on the effect of calcium flux agonists on IL-8 production and activation of NF-κB signaling. As can be readily taken from FIGS. 1A-1C, both ionophores and SERCA inhibitor produced significant increases in IL-8 production and activation of NF-κB signaling. The dose response is observed over relatively large windows for ionophores (e.g., A23187 and ionomycin) and over at least two orders of magnitude for SERCA inhibitors (e.g., thapsigargin).

Figure 1B:
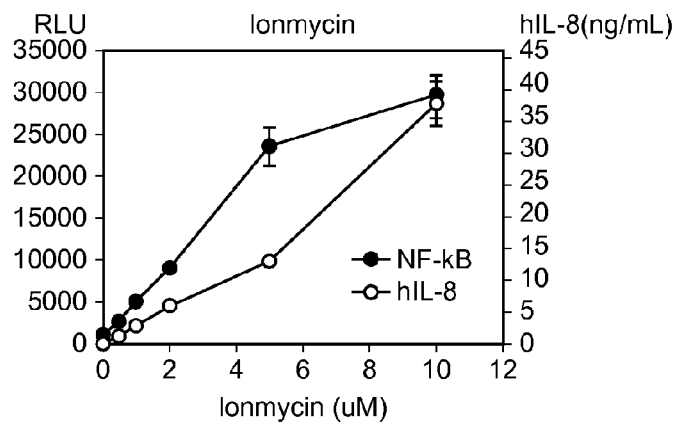
Figure 1C:
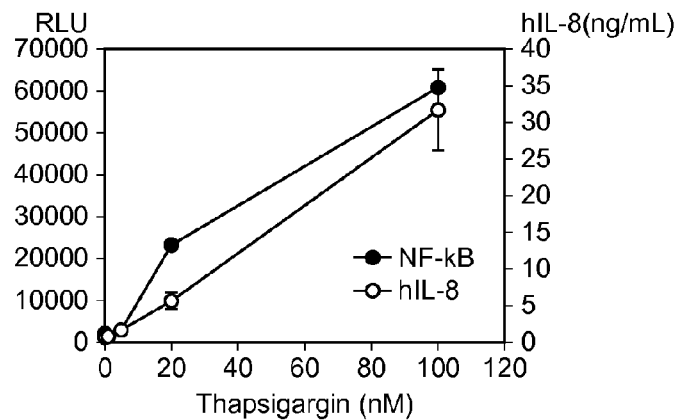

More specifically, the dose response of ionophores on NF-κB and IL-8 is shown in FIGS. 1A-1B using a monocyte-derived cell line to treatment and A23187 and ionomycin in the absence of externally added TLR or NOD ligands. A human monocytic cell line (THP-1) transfectant possessing a stably integrated NF-κB/luciferase reporter cassette was treated with increasing concentrations of A23187 and ionomycin and NF-κB reporter-based responses were monitored using luminometry (RLU=relative light units, filled circles) while human IL-8 (hIL-8) release was quantified using a sandwich ELISA (empty circles). FIG. 1C depicts the dose response to thapsigargin on NF-κB and IL-8. Here, the human monocytic cell line (THP-1) transfectant possessing a stably integrated NF-κB/luciferase reporter cassette was treated with increasing concentrations of thapsigargin and NF-κB reporter-based responses were monitored using luminometry (RLU=relative light units, filled circles) while human IL-8 (hIL-8) release was quantified using a sandwich ELISA (empty circles). As can be taken from both flux agonist groups, dose response is increasing over orders of magnitude at significantly increasing NF-κB and IL-8 responses.

Human IL-8 activity: A titration of thapsigargin (A.G. Scientific, San Diego Calif.), ionomycin (Sigma-Aldrich, St. Louis Mo.), and the calcium ionophore A23187 (Sigma-Aldrich) was added to a 96-well plate (Thermo Matrix, Waltham Mass.) seeded with 150,000 THP-1 cells (ATCC TIB-202) grown in RPMI 1640 (Cellgro, Herndon Va.) supplemented with 10% FBS (Thermo HyClone, Waltham Mass.) and 1% penicillin-streptomycin-fungizone (Thermo HyClone). 24 hours after addition, 25 µL of supernatant was removed and assayed for human IL-8 using the Meso Scale Discovery Human IL-8 Tissue Culture Kit (MSD, Rockville, Md.) per manufacturer's protocol. The results were analyzed using the Meso Scale Discovery SECTOR Imager 2400 and normalized to a titration of human IL-8 supplied by the MSD Kit.

NF-κB activation: A titration of thapsigargin (A.G. Scientific), ionomycin, and the calcium ionophore A23187 was added to a 96-well plate (Thermo Matrix) seeded with 150,000 THP-1 κB-LUC THP-1's (THP-1 cells containing the stable integration of a NF-κB Luciferase Reporter) grown in RPMI 1640 (Cellgro, Herndon Va.) supplemented with 10% FBS (Thermo HyClone) and 1% penicillin-streptomycin-fungizone (Thermo HyClone). 24 hours after addition, 25 µL of Bright-Glo Luciferase Assay System (Promega, Madison Wis.) was added to each well and analyzed for luciferase activity using Perkin Elmer TopCount NXT (Perkin Elmer, Waltham Mass.).

Calcium Flux Agonists as Synergistic Agents with Pattern Recognition Receptors

In an initial set of experiments, the TLR2 receptor ligand Pam2CYS was tested in the presence of various concentrations of calcium flux agonists and the inventors unexpectedly found that suboptimal and relatively low concentrations of a variety of calcium flux agonists in the presence of a TLR ligand produced a dramatic synergistic response.

Figure 2:
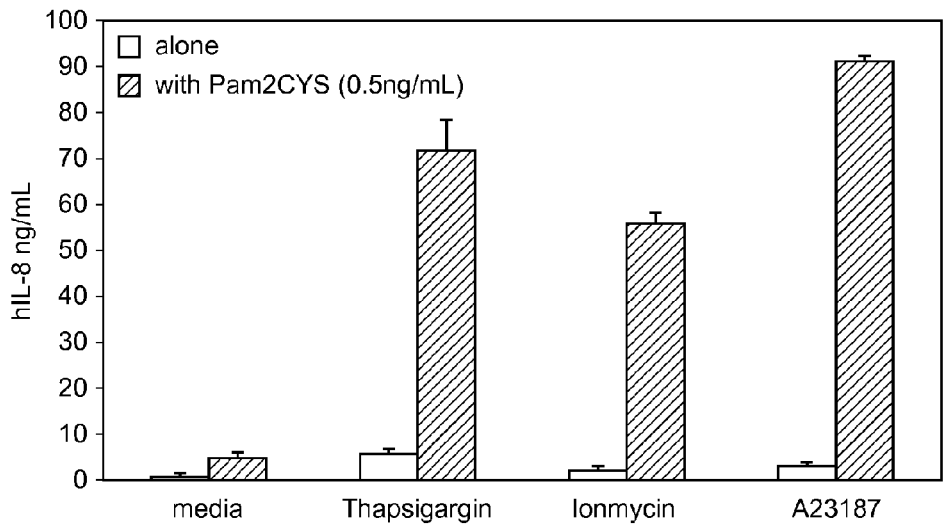
FIG. 2 is an exemplary graph depicting synergistic effect of various calcium flux agonists with an exemplary TLR ligand (Pam2CYS).

For example, FIG. 2 is a graph depicting a typical synergistic effect selected calcium flux agonists with an exemplary TLR ligand. Here, the ionophores A23187 and ionomycin, as well as the SERCA inhibitor thapsigargin synergize with the TLR2 ligand (Pam2CYS) in the activation of cytokine release from the human THP-1 promonocytic leukemia cell line. It should be especially noted that while the TLR2 ligand alone provided for about 5 ng/ml IL-8 response, addition of a suboptimal dose of the calcium flux agonists (e.g. 20 nM for thapsigargin, 316 nM for A23187, and 1 µM for ionomycin) produced more than 10-fold quantities of IL-8 production in the cells.

To investigate if that observation was also true for other pattern recognition receptors, and especially for TLR and NOD receptors and other ligands, the inventors tested numerous TLR and NOD receptors and various ligands. Notably, as is evidenced from FIGS. 3A-3E, substantial synergy was observed across a large selection of types and classes of calcium flux agonists, as well as various TLR and NOD receptors and ligands, thus establishing that TLR- and NOD-mediated signals can be (typically synergistically) enhanced with suboptimal dosages of calcium flux agonists.

Figure 3A:
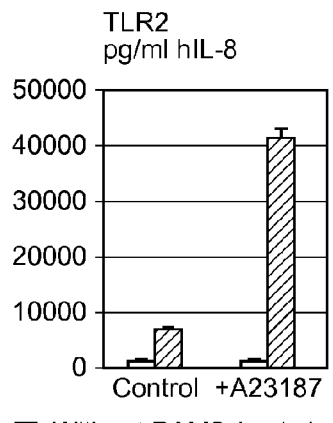
FIGS. 3A-3E show various graphs illustrating the synergistic effect of exemplary calcium flux agonists (FIG. 3A: A23187.
Figure 3A:
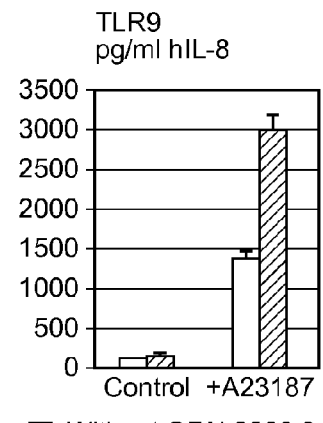
Figure 3A:
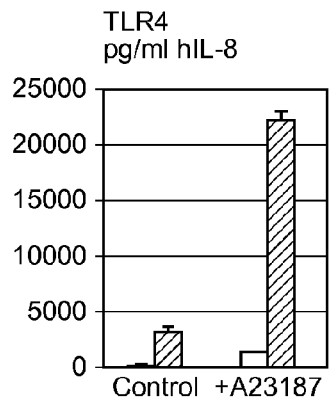
Figure 3A:
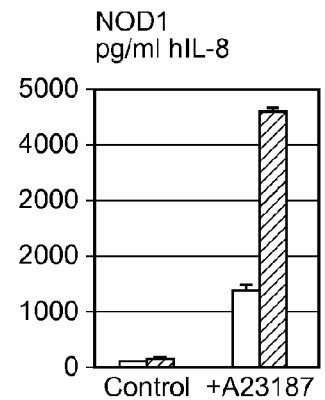
Figure 3A:
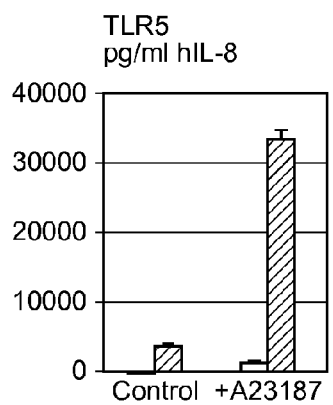
Figure 3A:
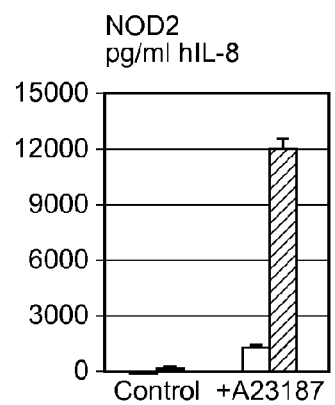
Figure 3B:
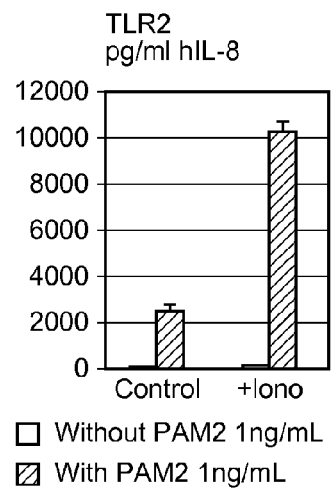
Figure 3B:
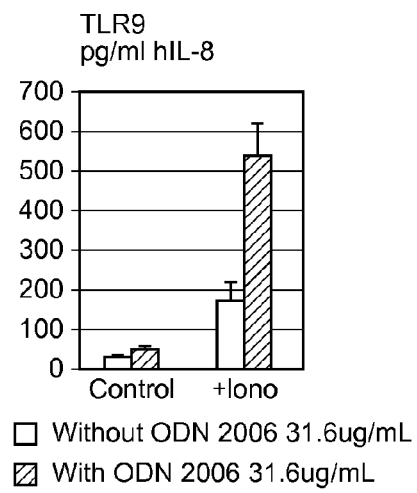
Figure 3B:
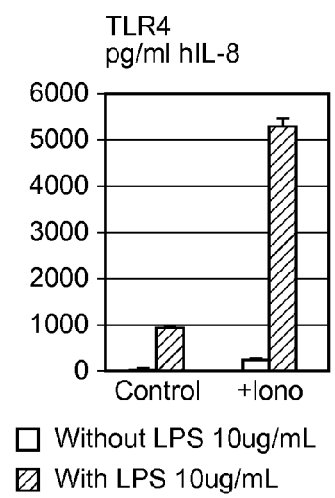
Figure 3B:
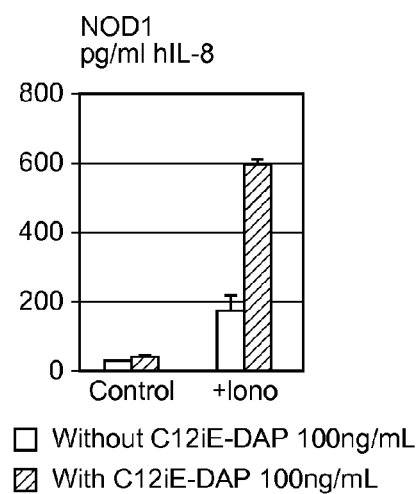
Figure 3B:
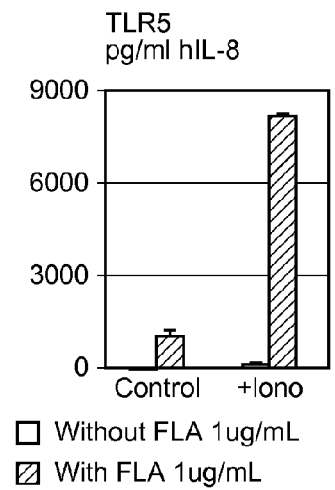
Figure 3B:
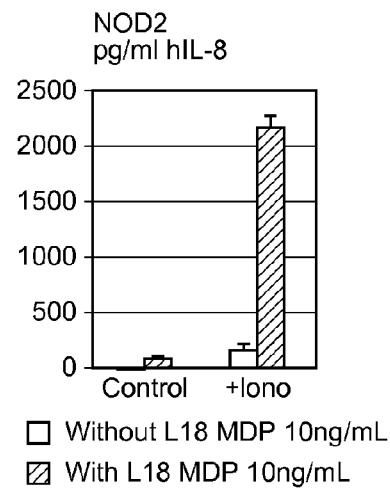
Figure 3C:
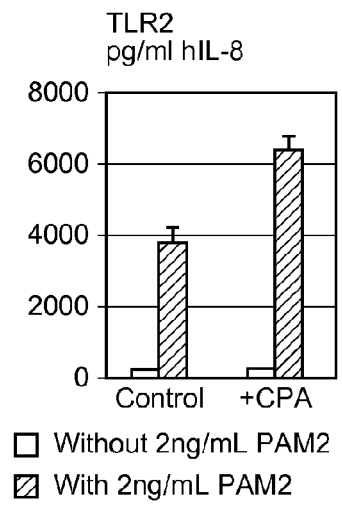
Figure 3C:
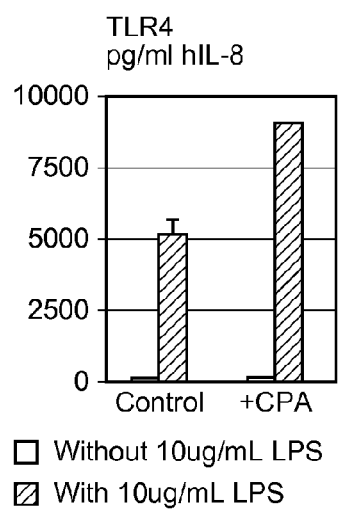
Figure 3C:
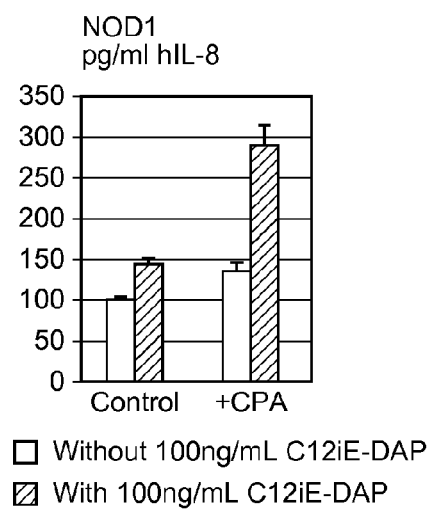
Figure 3C:
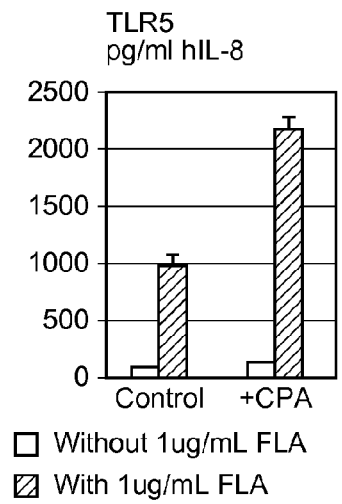
Figure 3C:
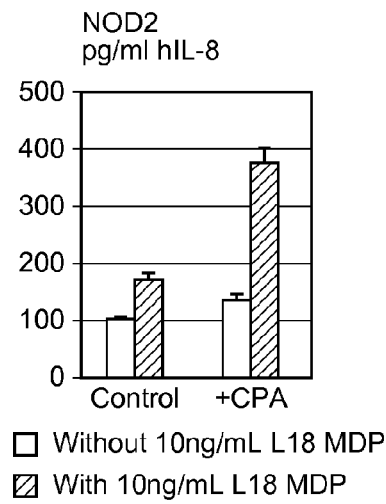
Figure 3D:
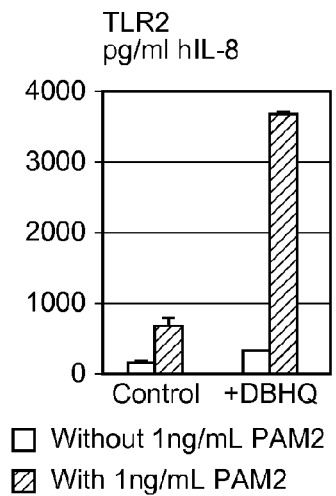
Figure 3D:
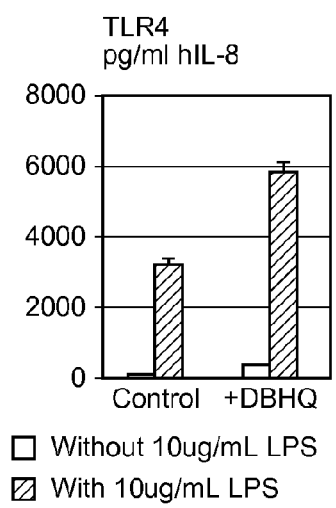
Figure 3D:
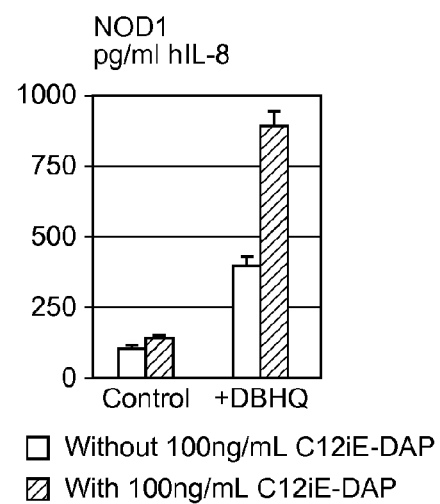
Figure 3D:
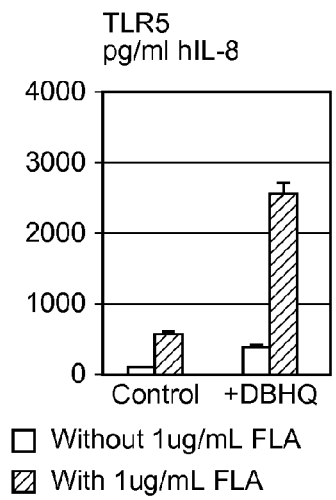
Figure 3D:
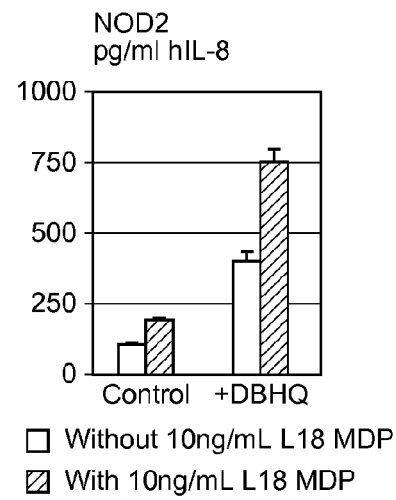
Figure 3E:
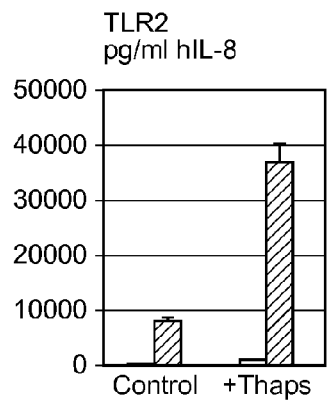
Figure 3E:
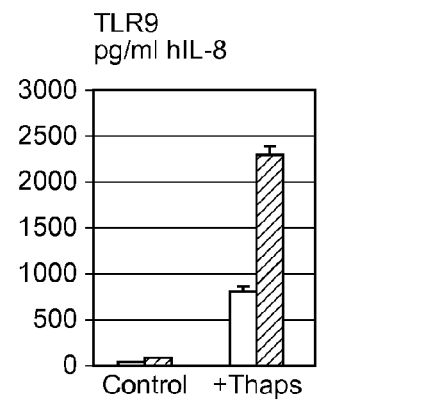
Figure 3E:
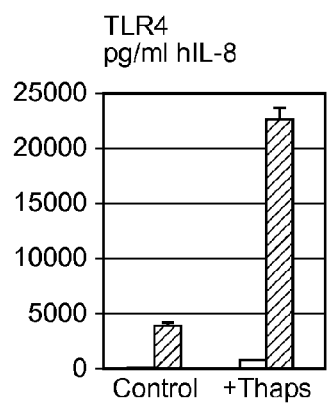
Figure 3E:
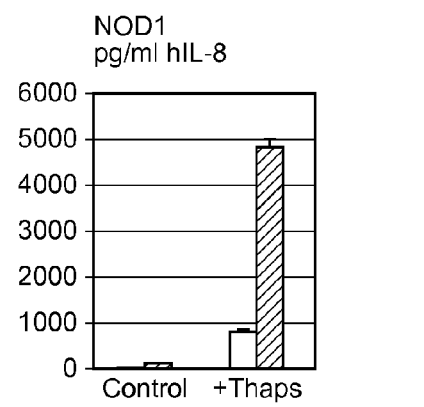
Figure 3E:
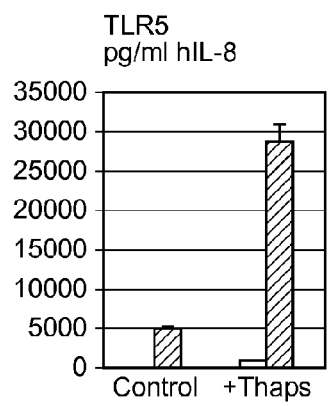
Figure 3E:
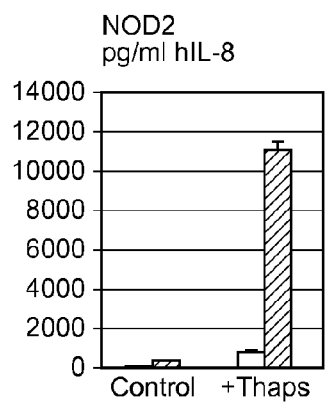

More specifically, FIG. 3A shows graphs depicting the synergistic effect of suboptimal doses of A23187 to augment cellular response for toll-like receptor (TLR) family members (TLR2, TLR4, TLR5, TLR9), and NOD family members (NOD1, NOD2). FIG. 3B shows graphs depicting the synergistic effect of suboptimal doses of ionomycin to augment cellular response for toll-like receptor (TLR) family members (TLR2, TLR4, TLR5, TLR9), and NOD family members (NOD1, NOD2). FIG. 3C shows graphs depicting the synergistic effect of suboptimal doses of cyclopiazonic acid to augment cellular response for toll-like receptor (TLR) family members (TLR2, TLR4, TLR5), and NOD family members (NOD1, NOD2). FIG. 3D shows graphs depicting the synergistic effect of suboptimal doses of 2,5-di(tert-butyl) hydroquinone (DBHQ) to augment cellular response for toll-like receptor (TLR) family members (TLR2, TLR4, TLR5), and NOD family members (NOD1, NOD2). FIG. 3E shows graphs depicting the synergistic effect of suboptimal doses of thapsigargin to augment cellular response for toll-like receptor (TLR) family members (TLR2, TLR4, TLR5, TLR9), and NOD family members (NOD1, NOD2). The doses used in this experiment were 20 nM for thapsigargin, 316 nM for A23187, 1 µM for ionomycin, 10 µM for cyclopiazonic acid, and 31.6 µM for DBHQ.

As can be readily appreciated, the synergistic effect with respect to IL-8 production was observed for all of the tested TLR and NOD family members and suitable ligands, while all of the tested calcium flux agonists were used at suboptimal concentration. Thus, a clear pattern of adjuvant activity of calcium flux agonists on the immune response, and especially on IL-8 production and NF-κB signaling is evident where the immune response is associated with a TLR- or NOD-mediated event.

Nature of Calcium Flux

Figure 4:
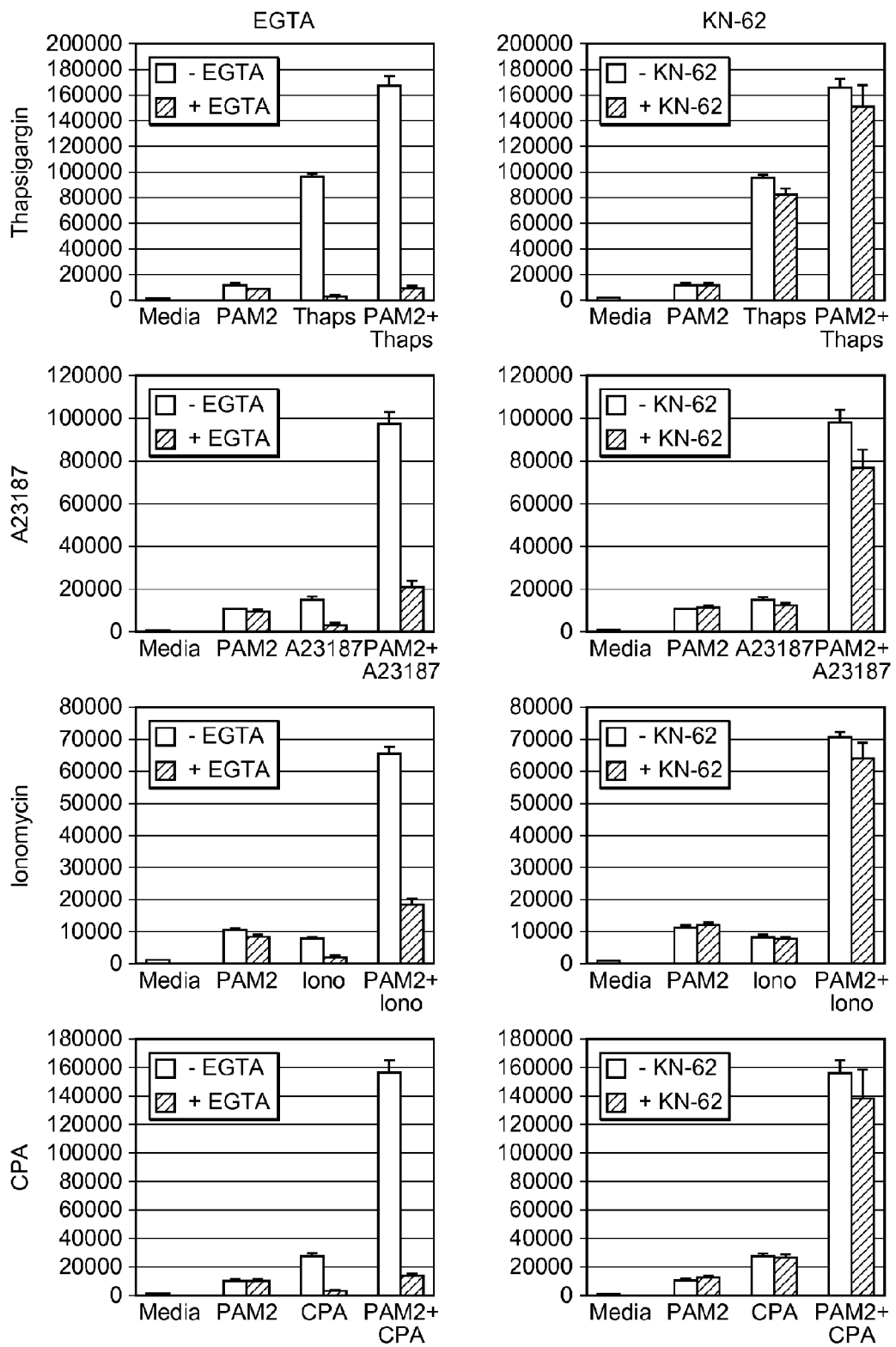
FIG. 4 shows graphs illustrating the effect of different $Ca^{2+}$ modulating compounds on the synergistic action with respect to NF-κB activation.

The inventors further investigated if the nature of calcium flux was of significance as increased intracellular calcium may have different origins. To that effect, the inventors used various calcium signaling modulators to investigate the nature of the calcium flux and contribution. As can be readily taken from the data shown, extracellular calcium flux into the cell was critical for synergistic amplification of calcium signaling. More specifically, FIG. 4 illustrates the effects of different $Ca^{2+}$ modulating compounds on synergy with respect to NF-κB activation. It should be noted that EGTA is an extracellular chelator, and that KN-62 is an inhibitor of Cam Kinase II (important for T-cell activation) that does not have chelator effect. As can be readily appreciated from FIG. 4, the extracellular $Ca^{2+}$ scavenger EGTA reduces synergistic signal down to levels in line with what is achieved by TLR ligand alone while treatment with the Cam Kinase II inhibitor KN-62 does not alter reporter gene expression levels.

Figure 5A:
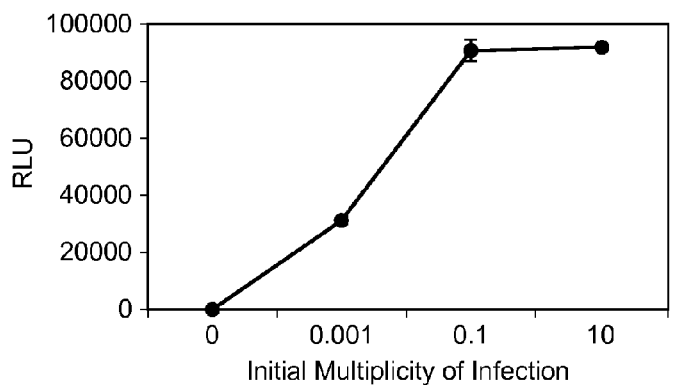
FIGS. 5A-5E show graphs depicting the effect of live bacterial growth on κB-LUC THP-1 reporter cells (FIG. 5A), augmentation of NF-κB response by thapsigargin (FIG. 5B), and the extracellular requirement of $Ca^{2+}$ for calcium flux agonist signal amplification (FIGS. 5C-5E).

Previously, it was demonstrated that TLR2 and NOD2 play important roles in the sensing and control of *S. aureus* infections by mammalian cells. Given that THP-1-derived κB-LUC THP-1 cells were activated by the generic TLR2 and NOD2 ligands Pam2Cys and MDP, respectively, and that this activation could be further augmented through the addition of calcium flux agonists (FIGS. 3A-3E), the ability of these cells to recognize bona fide *S. aureus*-derived products was evaluated as follows. Briefly, a culture of logarithmically dividing *S. aureus* was washed three times with RPMI 1640 (Cellgro). Concurrently, THP-1 κB-LUC THP-1's (THP-1 cells containing the stable integration of a NF-κB luciferase reporter gene) cultured in RPMI 1640 (Cellgro) supplemented with 10% FBS (Thermo HyClone, Waltham Mass.) and 1% penicillin-streptomycin-fungizone (Thermo HyClone) were washed three times with RPMI 1640 (Cellgro) and transferred to the bottom compartment of a 24-well 0.4 µm cutoff transwell plate (Corning) at a concentration of 1.2 million/mL. Dilutions of the washed *S. aureus* culture were then added to the top chamber of the transwell system at the indicated initial multiplicities of infection (MOI). The cells were incubated for 18 hours at 37° C. at which time aliquots of 60,000 cells were transferred to wells in a 384-well white bottom plate (Thermo). To evaluate luciferase gene expression, Bright-Glo Luciferase Assay Reagent (Promega) was added to each well and the plates were analyzed for luciferase activity using the Perkin Elmer TopCount NxT system (Perkin Elmer). Consistent with the previous results, the κB-LUC THP-1 reporter cells demonstrate a MOI-dependent increase in reporter activity when co-cultured with live bacteria in an culture system which allows for passive diffusion of bacterial products but prevents direct contact between whole *S. aureus* bacteria and the κB-LUC THP-1 reporter cells (FIG. 5A).

Figure 5B:
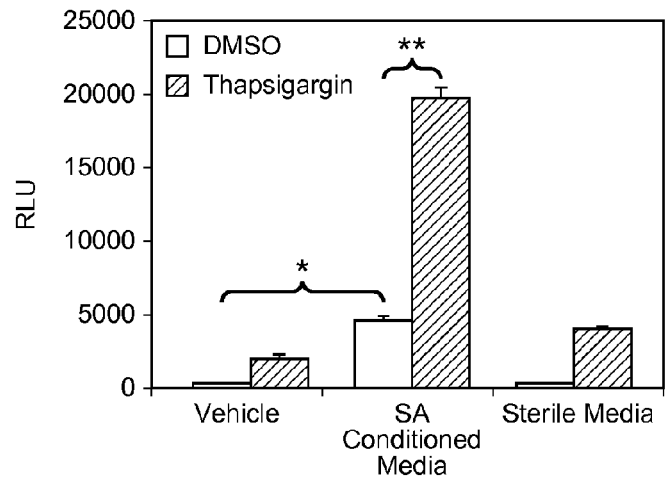

To determine whether the recognition of *S. aureus*-produced products could be further augmented through modulation of calcium flux, κB-LUC THP-1 reporter cells were incubated in the presence of a 1:100 dilution (V/V) of sterile filtered *S. aureus* conditioned (i.e. spent) or unused sterile media and treated with a suboptimal dose (20 nM) of thapsigargin or dimethyl sulfoxide (DMSO) vehicle control as described above. Briefly, conditioned media was produced by culturing *S. aureus* in RPMI with 10% fetal bovine serum overnight in a shaking incubator at 37° C. following which the bacteria were pelleted by centrifugation and the supernatants filter-sterilized using a 0.2 µm filter (VWR Radnor Pa.). The κB-LUC THP-1 cells were incubated in the presence of the conditioned/spent media for 18 hours prior to luciferase assay as described above. Interestingly, the response of the κB-LUC THP-1 reporter cells to the conditioned/spent bacterial culture was significantly enhanced in the presence of thapsigargin (FIG. 5B).

Figure 5C:
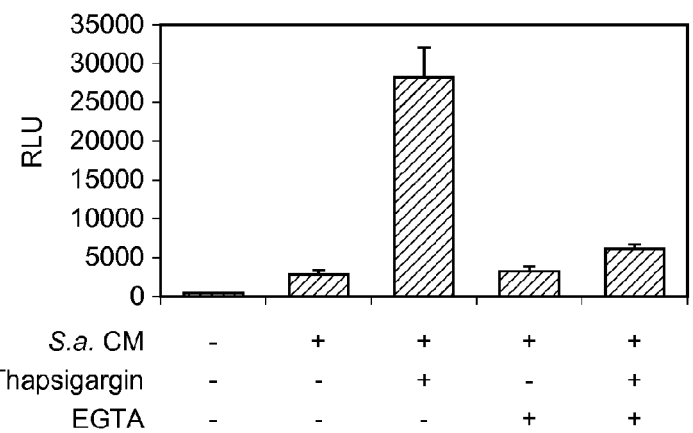
Figure 5D:
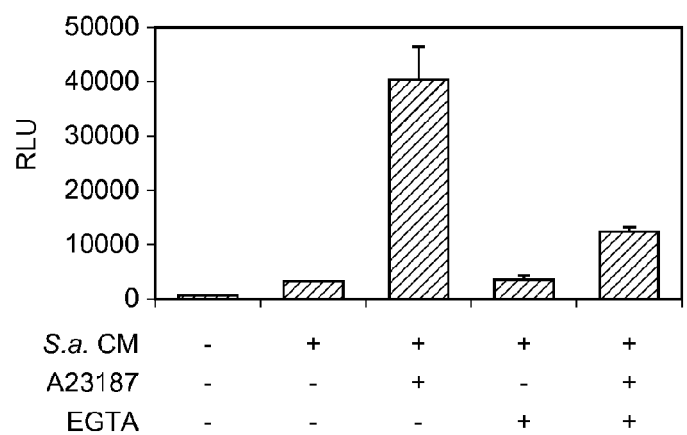
Figure 5E:
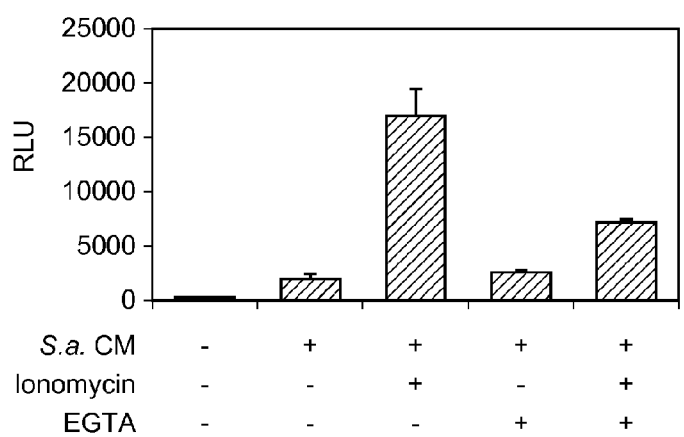

To determine whether the observed enhancement in activation of κB-LUC THP-1 cells by bacterial products achieved by suboptimal thapsigargin treatment was also true for the calcium ionophores A23187 and ionomycin, the experiment was repeated using these ionophores at the suboptimal doses of 316 nM and 1 µM, respectively. In all three cases, recognition of *S. aureus* conditioned/spent media was significantly enhanced in the presence of any of the calcium flux agonists (FIGS. 5C-5E). Perhaps of equal interest, the calcium flux-induced synergy could be inhibited by the addition of the extracellular chelator EGTA (1 mM) as can be readily seen form the Figures.

Role of Extracellular Calcium in Human Cells

To investigate whether the response in human cells is affected by the nature of the calcium flux, the inventors tested primary human monocytes and granulocytes infected with *S. aureus*. As can be seen from the data in FIG. 6, there is a clear requirement of human primary monocytes and granulocytes for extracellular $Ca^{2+}$ for optimal killing of phagocytosed *S. aureus*. Briefly, primary human monocytes were purified from a commercially available peripheral blood mononuclear cell preparation (Human Buffy Coat Leukocytes, Innovation Research, Novi Mich.) using the Dynabeads Untouched Human Monocyte kit (Life Technologies, Grand Island, N.Y.) per manufacturer's suggestions. Primary human granulocytes were purified by separating normal donor blood into two fractions by Ficoll-Paque density centrifugation by manufacturer's directions (GE Healthcare Life Sciences, Piscataway, N.J.). The peripheral blood mononuclear cell fraction was then discarded and the erythrocyte/granulocyte fraction was subjected to Red Blood Cell Lysis Buffer treatment per manufacturer's protocol (Biolegend, San Diego Calif.) followed by two washes in Hank's Buffered Salt Solution (Cellgro) to remove the lysis reagent and cell debris. Next, a culture of S. aureus was grown overnight in tryptic soy broth (Cellgro). The resulting culture was used to inoculate a new culture to ensure log phase growth prior to the start of the experiment. The bacterial culture was pelleted (2000×g for 10 min) and washed three times with Hank's Buffered Salt Solution (Cellgro). Primary monocytes/granulocytes prepared as above were then supplemented with 10% human serum (Innovative Research, Novi Mich.) and 1 mM EGTA (Sigma-Adrich, St. Louis Mo.) where applicable and chilled on ice for 30 minutes. After the 30 minutes, S. aureus (MOI of 3.33) was added and the mixtures were incubated on ice for an additional 20 minutes to synchronize binding. Tubes were then incubated for 20 minutes at 37° C. After 20 minutes, 10 U/mL of lysostaphin (Sigma-Aldrich) was added to each tube to eliminate non-internalized S. aureus. At the desired time points (20, 30, 60 minutes) 20 uL aliquots were removed and diluted in 10 mL of water. The dilution tubes were vortex and allowed to sit at room temp for 10 minutes to ensure proper lysis of the primary cells. After 10 minutes, the dilution tubes were centrifuged for 10 minutes at 2000×g with the remaining S. aureus was concentrated 20 fold. The S. aureus-containing samples were then plated in triplicate on tryptic soy agar (Cellgro) and incubated overnight at 37° C. to allow colony enumeration the following day.

In Vivo Models on Infection and Wound Healing

As already noted above, calcium flux agonists synergize with TLR and NOD ligands to activate pathways relevant to immune activation. Given the prevalence of TLR and NOD ligands in infection and injury, the inventors therefore contemplate that introduction of calcium flux agonists in these contexts will greatly decrease the duration of disease and/or augment repair function. To substantiate such model, various calcium flux agonists were tested in a pre-infection treatment experiment in their ability to alter wound healing kinetics and impact bacterial clearance.

Figure 8:
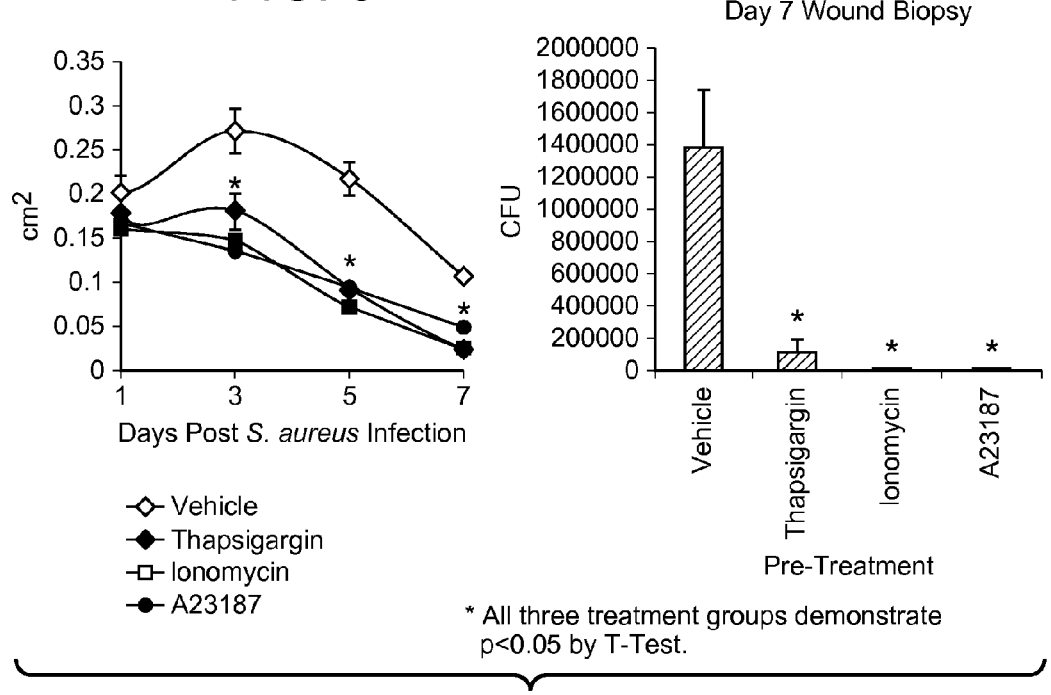
FIG. 8 shows graphs indicating wound size and bacterial burden following wound treatment with control and selected calcium flux agonists.

To determine if calcium flux agonists such as the ionophores A23187 and ionomycin or the SERCA pump inhibitor thapsigargin can be used as a pre-treatment of bacterial infection, the inventors treated the shaved dorsal skin of 6-8 week old male C57Bl/6 mice with vehicle alone, or formulations containing 2 mM A23187, ionomycin, or thapsigargin. One day later, the inventors superficially infected the dorsal skin of groups of 5 mice with $2\times10^6$ CFU of S. aureus and evaluated bacterial burden and wound size over the next week. Using this model, the inventors investigated if the calcium flux agonists would have a beneficial effect on wound healing (as measured by size) as demonstrated in FIG. 7. Interestingly, animals treated with either ionophore or thapsigargin demonstrated significantly smaller wound sizes (p<0.01 as determined by Student's T-test) on days 3, 5 and 7 of infection as compared to control treated animals. Furthermore, animals pre-treated with formulations containing either ionophore or thapsigargin possess significantly fewer bacteria at the infection site on day 7 compared to vehicle controls (FIG. 8).

Topical delivery: A23187 and ionomycin and thapsigargin were reconstituted in dehydrated ethanol (Spectrum Chemicals, Gardena Calif.) to appropriate concentrations for subsequent formulations. In the pre-infection in vivo study, topical formulations consisted of 75% dehydrated ethanol (Spectrum Chemicals), 22% cyclohexane (Sigma-Aldrich), and 3% dimethyl sulfoxide (Sigma-Aldrich). Each topical formulation was delivered by submersing a circular piece of Whatman paper (Whatman, a division of GE Healthcare) with a 1.0 centimeter diameter and applying said circle to the skin of each recipient for 5 minutes.

Preparation of S. aureus for skin inoculation: Briefly, mid-logarithmic phase S. aureus bacteria was washed twice and resuspended in sterile saline (0.9%) at the noted concentrations. Mice: Male mice, 6-8 weeks old, on a C57BL/6 genetic background were used in all experiments (Jackson Laboratories, Bar Harbor, Me.).

Mouse model of S. aureus skin wound infection: To prepare animals for wound infection, the skin of the posterior upper back and neck of mice was shaved using #40 clippers. Next, three parallel 8 mm long full-thickness scalpel cuts (no. 11 blade) were made into the dermis. Resulting wounds were inoculated with 10 µl of S. aureus ($2\times10^8$ CFUs per mL) with a micropipettor. Total lesion size (cm2) measurements were quantified by determining total pixel count from photographed animals using a millimeter ruler as a reference.

Quantification of in vivo S. aureus bacterial burden: To determine in vivo bacterial burden, infected mice were sacrificed on day 7 following infection and lesions were harvested surgically. Harvested tissues were homogenized and bacterial count was determined following plating on appropriate solid growth media.

Antibacterial Effect

Consistent with these and previous results regarding their inherent antibiotic activity against S. aureus, the inventors confirmed the direct antibiotic activity of both ionophores for direct antibiotic activity on methicillin-sensitive S. aureus (MSSA). As would be predicted, both ionophores were active against MSSA in a liquid culture assay with A23187 being the more active compound. Interestingly, both compounds demonstrated significant antibiotic activity against a methicillin-resistant S. aureus (MRSA) strain.

Figure 9C:
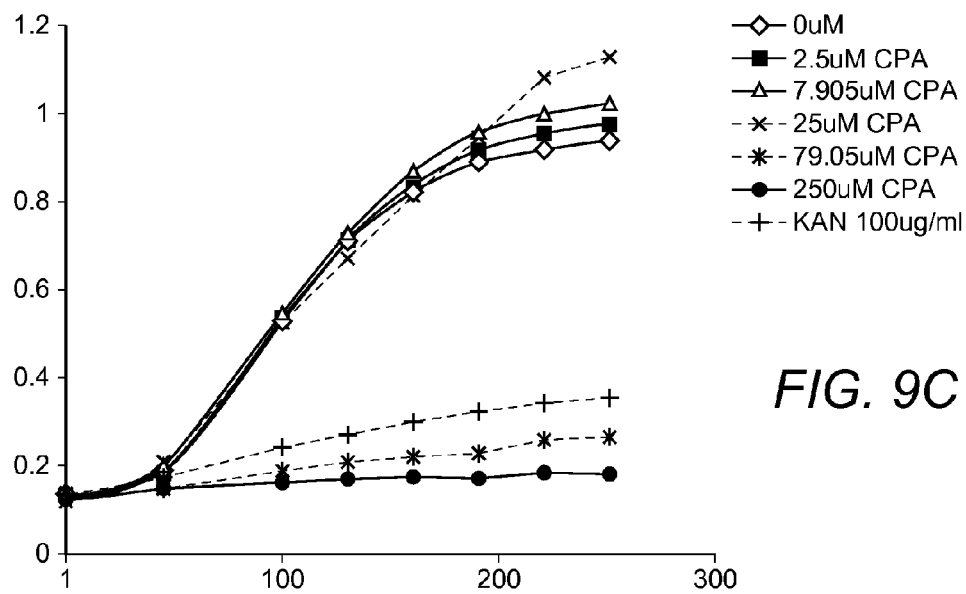
FIGS. 9A-9C show graphs for antibiotic sensitivity of S. aureus against A23187, ionomycin, and CPA, respectively.
Figure 9A:
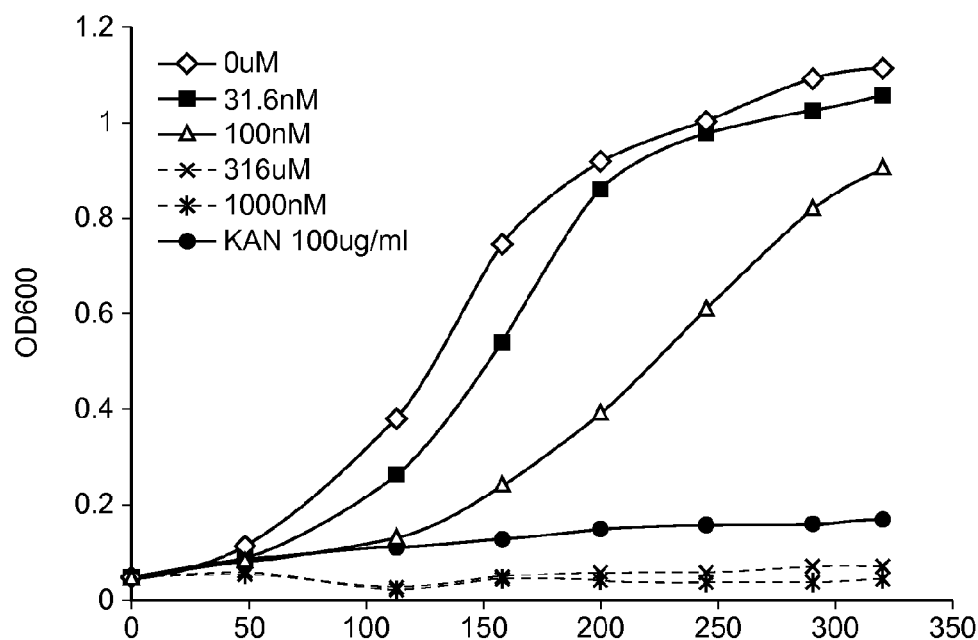
Figure 9A:
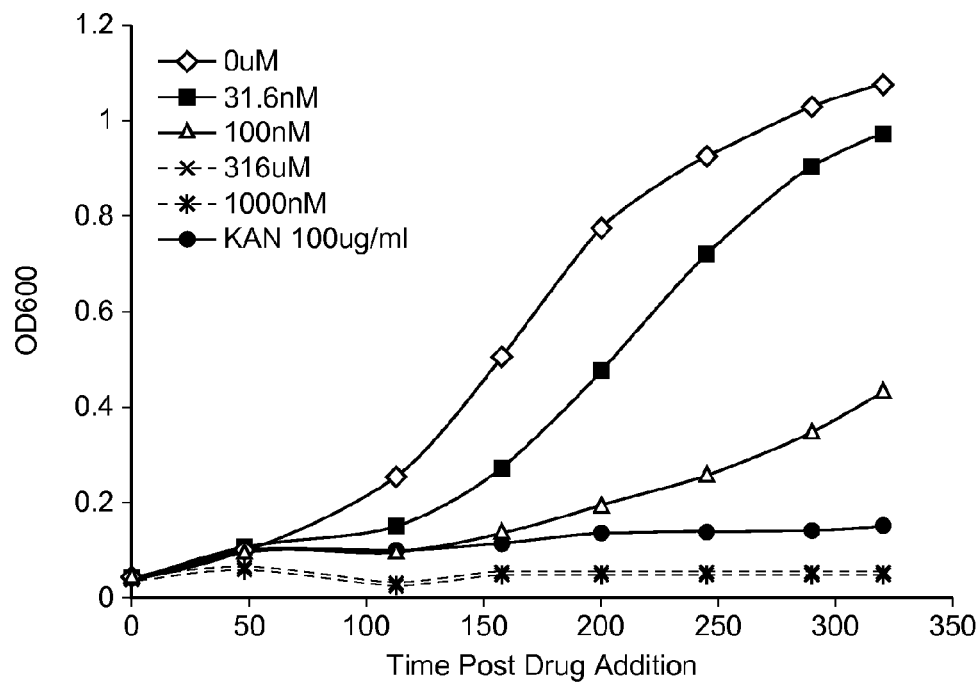
Figure 9B:
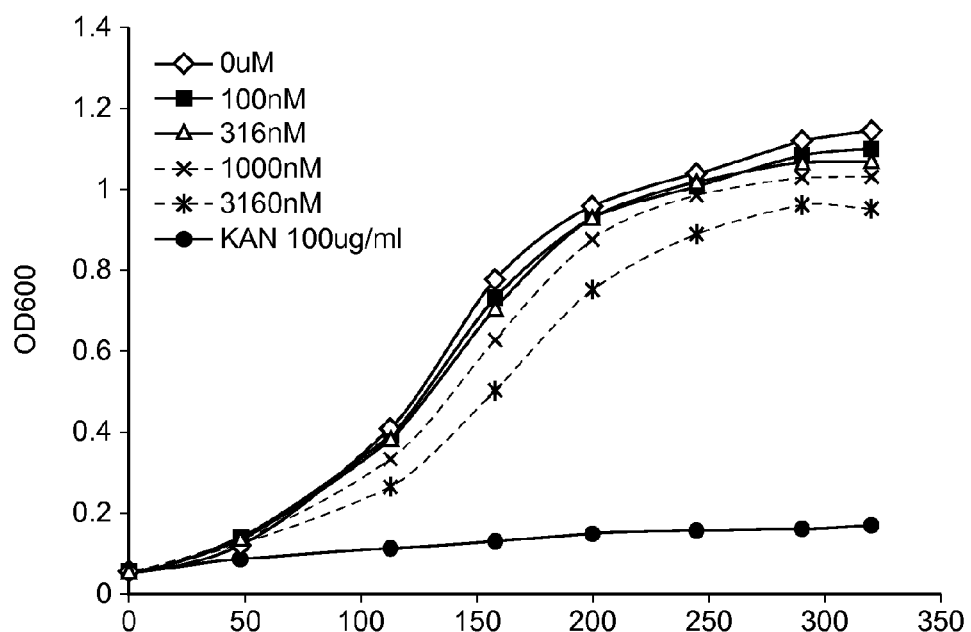
Figure 9B:
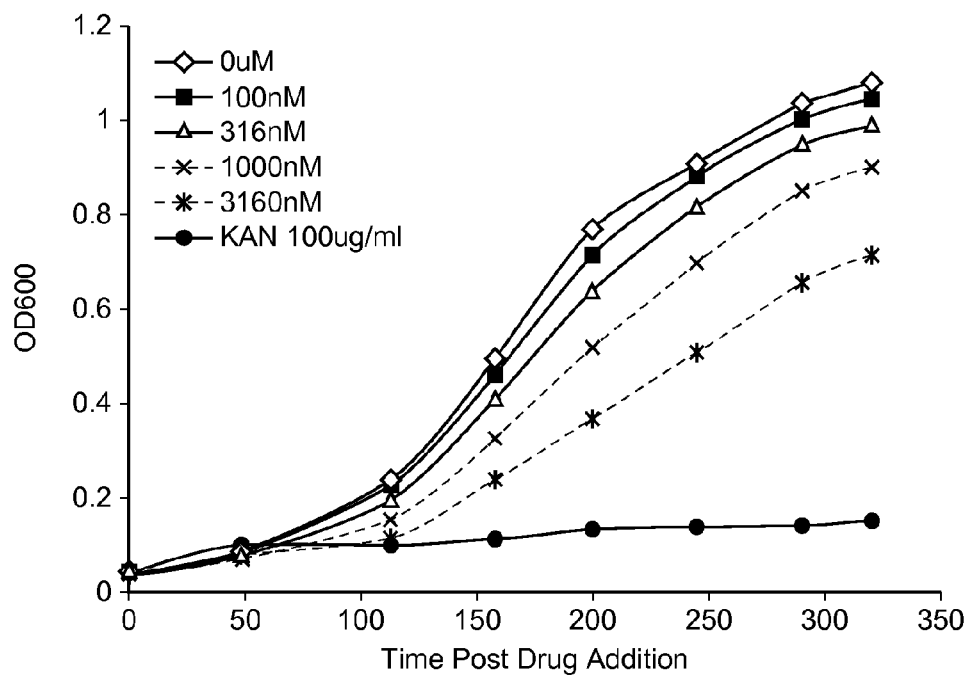
Figure 10:
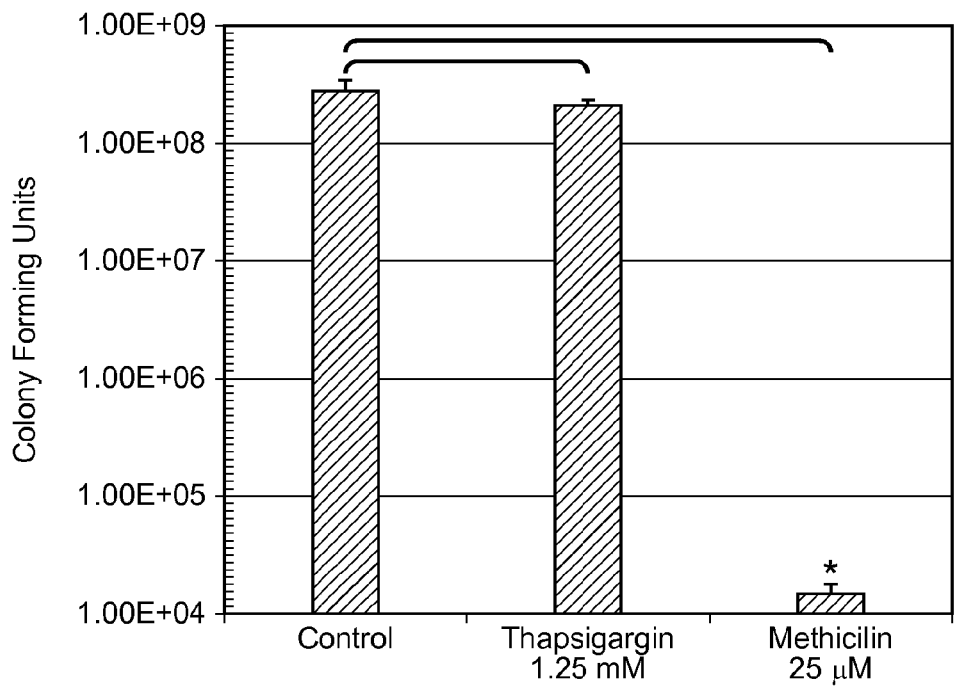
FIG. 10 is a graph depicting lack of direct antibiotic effect of thapsigargin against S. aureus.

For example, FIGS. 9A and 9B are graphs showing the antibiotic sensitivity of S. aureus against A23187 and ionomycin, respectively, and FIG. 9C shows antibiotic sensitivity of S. aureus against CPA. As can be taken from the graphs, both ionophores had some direct antibiotic effect, however, that effect was substantially less than the control using kanamycin as direct antibiotic. In contrast, FIG. 10 is a graph depicting lack of direct antibiotic effect of the SERCA inhibitor thapsigargin against S. aureus, even at high concentrations. To determine the antibiotic sensitivity of S. aureus, cultures were grown overnight in tryptic soy broth (Cellgro). The resulting cultures were used to inoculate new cultures to ensure log phase growth prior to the start of the experiment. Once the bacteria had reached log phase the bacteria was diluted to the appropriate $OD_{600}$~0.05 and transferred to a 24-well plate. Compounds of interest were added and plates were incubated in a shaking incubator at 37° C. Aliquots were removed at various time points and their respective $OD_{600}$ was measured using a BioTek Synergy2 microplate reader (BioTek, Winooski, Vt.). For wells whose turbidity was affected by the addition of the compounds of interest, aliquots were removed and plated on tryptic soy agar (Cellgro) and incubated overnight in a 37° C. incubated and counted the following day. Thus, it should be appreciated that the calcium flux agonists are effective in antimicrobial treatments via an indirect effect, most likely due to the enhanced production of IL-8 and increased NF-κB-driven transcription.

Figure 11:
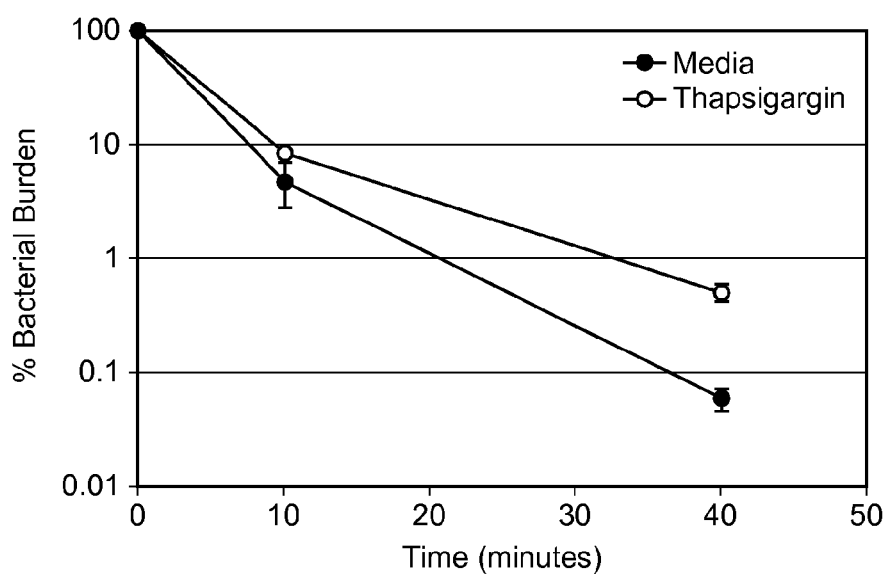
FIG. 11 is a graph showing improved killing of intracellular S. aureus by thapsigargin-treated cells.

Moreover, the inventors also discovered that the indirect antibiotic effect can be used in a prophylactic manner. For example, the inventors demonstrate that the promonocytic THP-1 cells treated thapsigargin displayed greater antimicrobial activity than similarly matured cells not treated with thapsigargin (FIG. 11). Briefly, a logarithmically dividing S. aureus was pelleted (2000×g for 10 min) and washed three times with Hank's Buffered Salt Solution (Cellgro). Concurrently, 2 day differentiated THP-1 cells (using 1 uM retinoic acid and 1 uM cholecalciferaol, Sigma-Aldrich) followed by 1 day with 20 nM thapsigargin or vehicle were collected and washed in Hank's Buffered Salt Solution. Differentiated cells were supplemented with 10% human serum (Innovative Research) and chilled on ice for 30 minutes. After the 30 minutes, S. aureus (MOI of 10) was added on ice for an additional 20 minutes to synchronize binding. Tubes were then incubated for 20 minutes at 37° C. After 20 minutes, 10U/mL of lysostaphin (Sigma-Aldrich) was added to eliminate non-internalized bacteria. At the desired time points (20, 30, 60 minutes) 20 uL aliquots were removed and diluted into 10 mL of water. The dilution tubes were vortex and allowed to sit at room temp for 10 minutes to ensure proper lysis of the primary cells. After 10 minutes, the dilution tubes were centrifuged for 10 minutes at 2000×g and the remaining S. aureus was concentrated 20 fold and plated in triplicate on tryptic soy agar (Cellgro) and incubated overnight at 37° C. prior to colony enumeration.

Consequently, it should be appreciated that one or more ionophores can be employed as topical prophylactic and/or therapeutic agents for treatment of skin infections and/or to improve wound healing. Of particular significance is the use of such compositions and methods in an immunostimulatory manner rather than in a direct antibiotic manner, which will advantageously avoids difficulties otherwise associated with resistance build-up due to antibiotic therapy. Of course, it should be appreciated that numerous other pathogens are also contemplated herein, and in fact include all currently known skin pathogens (bacterial, viral, parasitical, and fungal).

It should still further be appreciated that a significant synergistic effect was observed during treatment with contemplated compounds, where the synergy was between the ionophores and TLR ligands in activating immune cells. Such synergy could be of particular interest for treatments that are already directed to modification of immune response (e.g., drug therapy using Aldara) or other immune-activating therapies to combat disease. Therefore, the inventors contemplate that ionophores can be used therapeutically to combat superficial skin infections before and after onset. Moreover, and given the dual physical barrier and immunological functions of the skin and the wealth of in vitro data demonstrating the activating/modulating activities of the ionophores in immune cells, the inventors also contemplate that topical formulations containing ionophores will be of therapeutic benefit in patients requiring treatment for acute (e.g., from injury) or chronic (e.g., as observed in diabetic ulcers, etc) superficial wounds, burns, and other inflammatory/autoimmune disorders of the skin (e.g., psoriasis, eczema, etc).

Besides the skin, epithelial tissues include the cells lining the gastrointestinal tract (including the alimentary cavity), the respiratory tract and the urogenital tract. Other than the latter, the remaining tissues are constantly exposed to microorganisms and other factors such as pollen and man-made environmental pollutants, which can cause or otherwise exacerbate local inflammation and/or lesion formation. Due to the prevalence of microorganisms which activate TLR receptors throughout the gastrointestinal tract (including the mouth), it is also contemplated to utilize ionophores in the treatment of mouth abscesses and possibly inflammatory bowel disorders.

Consequently, it should be appreciated that topically-applied thapsigargin can be used as a treatment agent to synergize with TLR ligands in activating immune cells. Most notably, the inventors discovered that skin treated with thapsigargin or other calcium flux agonists prior to infection clears live bacteria and heals faster than control-treated skin, Of equal importance, the inventors showed that the differences observed in vivo are unlikely to be due to inherent antibiotic property of thapsigargin. As a result, the inventors contemplate that thapsigargin or other calcium flux agonists can be used therapeutically to combat superficial skin infections caused by pathogens that produce or contain TLR/NOD ligands (e.g., S. aureus) after their onset. Given the dual physical barrier and immunological functions of the skin and the wealth of in vitro data demonstrating the activating/modulating activities of thapsigargin or other calcium flux agonists in immune cells, the inventors contemplate that topical formulations containing thapsigargin are of therapeutic benefit in patients requiring treatment for acute (e.g., from injury) or chronic (e.g., as observed in diabetic ulcers, etc.) superficial wounds, burns, and other inflammatory/autoimmune disorders of the skin (e.g., psoriasis, eczema, etc).

Thus, specific embodiments and applications of calcium flux agonists have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A method of enhancing an immune response in skin of a topically applied medicament, comprising a step of including a calcium flux agonist in the medicament at a concentration effective to enhance the immune response in skin, wherein the immune response is associated with binding of a ligand to a pattern recognition receptor in an immune competent cell.

2. The method of claim 1 wherein the pattern recognition receptor is a TLR receptor or a NOD receptor.

3. The method of claim 1 wherein the calcium flux agonist is a calcium ionophore.

4. The method of claim 3 wherein the calcium ionophore is ionomycin, calcimycin, calcium ionophore II, calcium ionophore IV, calcium ionophore V, or calcium ionophore VI.

5. The method of claim 1 wherein the calcium flux agonist is a SERCA inhibitor.

6. The method of claim 5 wherein the SERCA inhibitor is 2,5-Di-tert-butylhydroquinone, thapsigargin, ruthenium red, gingerol, paxilline, or cyclopiazonic acid.

7. The method of claim 1 wherein the calcium flux agonist is present in the medicament at a concentration such that the calcium flux agonist is present in the cell in the presence of the ligand at a suboptimal concentration with respect to a maximum effect of the calcium flux agonist in the absence of the ligand.

8. The method of claim 1 wherein the enhanced immune response is increased IL-8 secretion or increased activation of NF-κB signaling.

9. The method of claim 1 wherein the immune competent cell is a cell residing in an epidermis or a dermis.

10. The method of claim 1 wherein the ligand of the pattern recognition receptor is a PAMP.

11. The method of claim 1 wherein the immune response is enhanced in a synergistic manner in the presence of the ligand, and wherein the calcium flux agonist is used in the presence of the ligand at a suboptimal concentration with respect to a maximum effect of the calcium flux agonist in the absence of the ligand.

12. The method of claim 1 wherein the skin is a wounded skin.

13. The method of claim 1 wherein the skin is a wounded skin infected with a bacterial pathogen.

* * * * *